US011255806B2

(12) United States Patent
Rajaraman et al.

(10) Patent No.: US 11,255,806 B2
(45) Date of Patent: Feb. 22, 2022

(54) INTERDIGITATED ELECTRODES FOR IN VITRO ANALYSIS OF CELLS

(71) Applicant: UNIVERSITY OF CENTRAL FLORIDA RESEARCH FOUNDATION, INC., Orlando, FL (US)

(72) Inventors: Swaminathan Rajaraman, Winter Park, FL (US); Jayan Thomas, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 431 days.

(21) Appl. No.: 16/166,836

(22) Filed: Oct. 22, 2018

(65) Prior Publication Data

US 2019/0162688 A1    May 30, 2019

Related U.S. Application Data

(60) Provisional application No. 62/574,935, filed on Oct. 20, 2017.

(51) Int. Cl.
*C12M 3/00* (2006.01)
*B01L 3/00* (2006.01)
(Continued)

(52) U.S. Cl.
CPC ......... *G01N 27/126* (2013.01); *C12M 1/3407* (2013.01); *C12M 1/42* (2013.01);
(Continued)

(58) Field of Classification Search
CPC ................. C12M 23/20; C12M 1/3407; B01L 2300/0645
See application file for complete search history.

(56) References Cited

U.S. PATENT DOCUMENTS

| 2008/0285039 | A1* | 11/2008 | Que | G01N 21/648 |
| | | | | 356/445 |
| 2009/0047485 | A1* | 2/2009 | Ofir | G03F 7/2059 |
| | | | | 428/206 |

(Continued)

OTHER PUBLICATIONS

Altissimo M., "E-beam lithography for micro-/nanofabrication". Biomicrofluidics, vol. 4, Issue 2, pp. 1-6 (2010).

(Continued)

*Primary Examiner* — Nathan A Bowers
(74) *Attorney, Agent, or Firm* — Timothy H. Van Dyke; Wolter, Van Dyke, Davis, PLLC

(57) ABSTRACT

Described are interdigitated electrodes, which may optionally be plasmonic, useful for in vitro biosensing applications. Such devices may significantly reduce undesired background noise by separating the excitation source (light) from the detection signal (current), and thereby, leading to higher sensitivity for bioanalysis compared with conventional interdigitated electrodes. Also described are methods of making such interdigitated electrodes, which allow a substrate, which may optionally be plasmonic, to be tuned not only to maximize the targeted interaction of the cells with the nanoscale geometry, but also for the excitation wavelength to minimize biological sample interference.

9 Claims, 25 Drawing Sheets

(51) Int. Cl.
  G01N 27/12   (2006.01)
  C12M 1/34    (2006.01)
  C12M 1/00    (2006.01)
  C12M 1/32    (2006.01)
  C12M 1/42    (2006.01)
  G01N 15/00   (2006.01)
(52) U.S. Cl.
  CPC ............ *C12M 23/12* (2013.01); *C12M 23/20* (2013.01); *C12M 41/46* (2013.01); *B01L 2300/0645* (2013.01); *G01N 2015/0065* (2013.01)

(56) References Cited

U.S. PATENT DOCUMENTS

| | | | | |
|---|---|---|---|---|
| 2009/0294303 | A1* | 12/2009 | Fischer | G01N 27/127 205/780.5 |
| 2012/0292496 | A1* | 11/2012 | Escobedo | G01N 33/54373 250/282 |
| 2017/0152549 | A1* | 6/2017 | Shih | G01N 33/54373 |
| 2017/0284935 | A1* | 10/2017 | Ndukaife | G01N 15/00 |
| 2018/0188230 | A1* | 7/2018 | Huff | B01L 3/502761 |
| 2019/0064139 | A1* | 2/2019 | Nawarathna | G01N 33/487 |

OTHER PUBLICATIONS

Cellular Dynamics Internaional, Inc., "iCell Cardiomyocytes User's Guide", Madison, pp. 1-19 (2016).
Chantharasupawong P., et al., "Coupling Enhancement and Giant Rabi-Splitting in Large Arrays of Tunable Plexcitonic Substrates", Journal of Physical Chemistry C, vol. 118 Issue 41, p. 23954-23962 (2014).
Chou S., et al., "Imprint of sub-25 nm vias and trenches in polymers", Applied Physics Letters, vol. 67, Issue 21, p. 3114-3116 (1995).
Contreras-Saenz M., et al., "Maskless fabrication of a microfluidic device with interdigitated electrodes on PCB using laser ablation", pp. 1-7 (2016).
Delle L., et al., "ScFv-modified graphene-coated IDE-arrays for 'label-free' screening of cardiovascular disease biomarkers in physiological saline", Biosensors and Bioelectronics, vol. 102, pp. 574-581 (2018).
Dimasi J., et al., "Innovation in the pharmaceutical industry: New estimates of R&D costs", Journal of Health Economics, vol. 47, pp. 20-33 (2016).
Duong B., et al., "Printed Sub-100 nm Polymer-Derived Ceramic Structures". ACS Applied Materials and Interfaces, vol. 5, Issue 9, p. 3894-3899 (2013).
Duong B., et al., "Enhanced Magnetism in Highly Ordered Magnetite Nanoparticle-Filled Nanohole Arrays", Small, vol. 10, Issue 14, pp. 2840-2848 (2014).
Guo L., et al., "Estimating the Risk of Drug-Induced Proarrhythmia Using Human Induced Pluripotent Stem Cell-Derived Cardiomyocytes", Toxixological Sciences, vol. 123, pp. 281-289 (2011).
Himmel H., "Drug-induced functional cardiotoxicity screening in stem-cell derived human and mouse cardiomyocytes: Effects on reference compounds", Journal of Pharmacological and Toxicological Methods, vol. 68, pp. 97-111 (2013).
Hu N., et al., "Comparison between ECIS and LAPS for establishing a cardiomyocyte-based biosensor", Sensors and Actuators B: Chemical, vol. 185, pp. 238-244 (2013).
Hu N., et al., "High-performance beating pattern function of human induced pluripotent stem cell-derived cardiomyocyte-based biosensors for hERG inhibition recognition", Biosensors and Bioelectronics, vol. 67, pp. 146-153 (2015).
Kovylina M., et al., "Tuning exchange bias in Ni/FeF2 heterostructures using antidot arrays", Applied Physics Letters, vol. 95, p. 1-3 (2009).
Krinke D., et al., "A microelectrode-based sensor for label-free in vitro detection of ischemic effects on cardiomyocytes", Biosensors and Bioelectronics, vol. 24, pp. 2798-2803 (2009).
Mazlan M., et al., "Interdigitated electrodes as impedance and capacitance biosensors: A review", Krabi, Thailand, p. 1-8 (2017).
Millard D., et al., "Cross-Site Reliability of Human Induced Pluripotent Stem-Cell Derived Cardiomyocyte Based Safety Assays Using Microelectrode Arrays: Results from a Blinded CiPA Pilot Study", Toxicological Sciences, pp. 550-562 (2018).
Pal S., et al., "Carbon nanostraws: nanotubes filled with superparamagnetic nanoparticles", Nanotechnology, vol. 20, p. 1-8 (2009).
Peterson S., et al., "Poly(dimethylsiloxane) thin films as biocompatible coatings for microfluidic devices: Cell culture and flow studies with glial cells", Journal of Biomedical Materials Research Part A, vol. 72, pp. 10-18 (2005).
Qian F., et al., "Simultaneous electrical recording of cardiac electrophysiology and contraction on chip", Lab on a Chip, vol. 17, Issue 10, pp. 1681-1846 (2017).
Qiu Y., et al., "Real-Time Monitoring Primary Cardiomyocyte Adhesion Based on Electrochemical Impedance Spectroscopy and Electrical Cell-Substrate Impedance Sensing", Analytical Chemistry, vol. 80, Issue 4, pp. 990-996 (2008).
Sokolov A., et al., "Complement activation by candidate biomaterials of an implantable microfabricated medical device", Journal of Biomaterials Research Part B, vol. 98, Issue 2, pp. 323-329 (2011).
Solly K., et al., "Application of Real-Time Cell Electronic Sensing (RT-CES) Technology to Cell-Based Assays", Assay and Drug Development Technologies, vol. 2, No. 4, pp. 363-372 (2004).
Stockman M., et al., "Roadmap on plasmonics", J. Opt., vol. 20, pp. 1-39 (2018).
Tandon N., et al., "Surface-Patterned Electrode Bioreactor for Electrical Stimulation", Lab on a Chip, vol. 10, Issue 6, pp. 692-700 (2010).
Wang H., et al., "Fabrication and magnetotransport properties of ordered sub-100 nm pseudo-spin-valve element arrays", Nanotechnology, vol. 17, Issue 6, pp. 1651-1654 (2006).
Wang T., et al., "A cardiomyocyte-based biosensor for antiarrhythmic drug evaluation by simultaneously monitoring cell growth and beating", Biosensors and Bioelectronics, vol. 49, pp. 9-13 (2013).
Williamson K., "Do both adrenaline and noradrenaline stimulate cardiac α-adrenoceptors to induce positive inotropy of rat atria?", British Journal of Pharmacology, vol. 98, Issue 2, pp. 597-611 (1989).
Yu Z., et al., "Dual-Function Coaxial Supercapacitor Cable", ECS Trans., vol. 61, Issue 18, pp. 31-36 (2014).
Zhou J., et al., "Assessment of cadmium-induced hepatotoxicity and protective effects of zinc against it using an improved cell-based biosensor", Sensors and Actuators A: Physical, vol. 199, pp. 156-164 (2013).

* cited by examiner

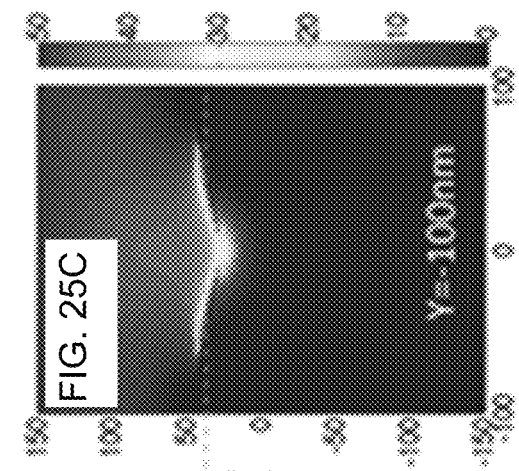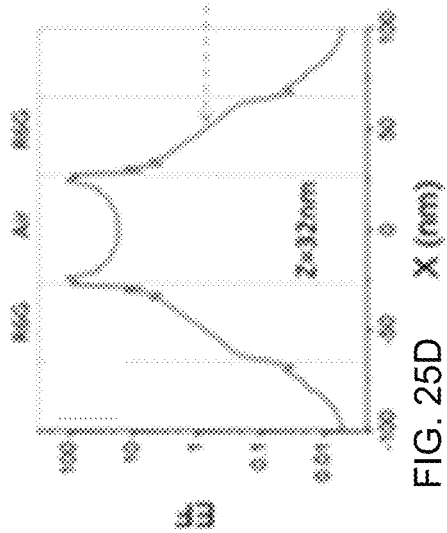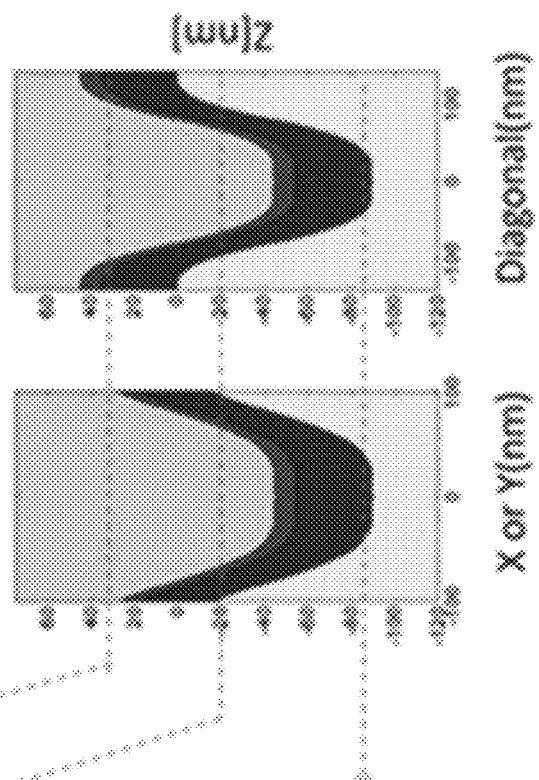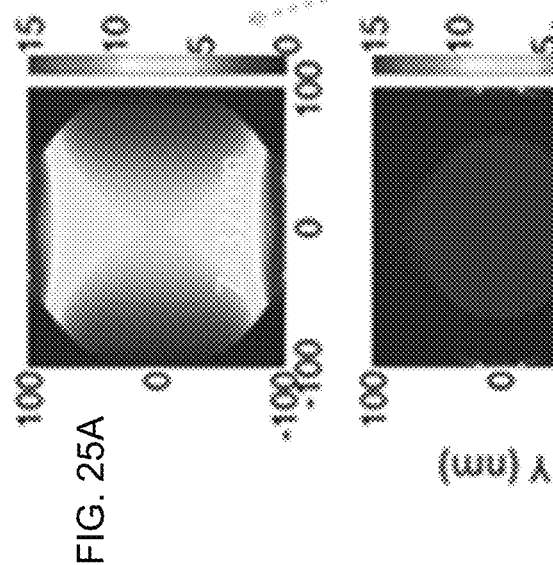

INTERDIGITATED ELECTRODES FOR IN VITRO ANALYSIS OF CELLS

CROSS-REFERENCE TO RELATED APPLICATION

This application claims the benefit of U.S. Provisional Patent Application No. 62/574,935, filed Oct. 20, 2017, titled Plasmonic Interdigitated Electrodes (PIEDs) for In vitro Analysis of Cells, which is incorporated by reference herein in its entirety.

BACKGROUND

Bioelectronics is a rapidly growing, interdisciplinary field that encompasses the integration of biomaterials, cells and tissue with electronic devices. Of the several devices utilized in this field, two important bioelectronic interfaces that are used extensively with electrogenic cells (neural or cardiac cells) are electrodes for electrical impedance spectroscopy and extracellular electrophysiological measurements. Both techniques are label-free methodologies for real-time monitoring of cellular interactions. Impedance spectroscopy measures the frequency-dependent alterations of passive electrical properties of networks of cells by applying defined AC currents or voltages. Since this is a non-invasive method, long-term effects on cellular behavior from external compounds can be realized without invasively entering the cells. Such devices have applications in several in vitro biosensing assays such as cellular proliferation, quality control of cells, compound mediated cytotoxicity, cellular adhesion, cellular morphology, functional monitoring of receptors and viral quantification. Several of these factors are required to be studied during the process of drug discovery both at the cellular network level and at a single cell level. Due to the extent of characterization and the long lead times with animal and human testing, bringing a drug to market is extremely expensive. In the realm of cardiac drugs, cardiotoxicity has been cited as a major reason for 30 percent of all failed drug compounds during development and is a major cause of compound attrition. Early scale detection of the cardiotoxic side effects of drug compounds prevents the disqualification of these compounds at a later stage and as a result reduces the cost and the time to adopt these new pharmacological compounds.

Traditional analysis of the cardiotoxicity of drug compounds has involved ex vivo or in vivo studies with the isolation of these compounds in animal models such as rats and pigs and the electrophysiological and viability studies on the isolated cardiomyocytes. Alternative and newer methodologies rely on in vitro cell-based assays that express specific ion channels in the cardiomyocytes such as the hERG channel or the voltage gated calcium channel. These ion channels serve as possible molecular targets through which the drug compound could induce cytotoxicity and are typically studied with techniques such as patch clamping that are invasive and may lead to cell death after the implementation of the technique. Microelectrode Arrays (MEAs) and impedance arrays are non-invasive, label-free technologies that may be utilized to track the cardiotoxicity of compounds outside the animal model in vitro and in a dish empowering the researcher with greater experimental control. These devices typically have a grid of thin film metal and insulation typically defined on substrates such as glass and silicon in the case of MEAs and a whole variety of interdigitated electrode designs of different thin films defined on mostly transparent substrates in the case of impedance arrays. The interdigitated electrodes (IDEs) report a change in extracellular electrophysiological signature or a change in impedance as the output signal correlated to a change in behavior of a group of cardiomyocytes cultured on the electrodes. Single cell or single ion channel accuracy evades these sensors without complex technologies such as nanoimprint lithography or e-beam lithography that make these sensors unaffordable to most users.

Furthermore, drug-induced cardiotoxicity accounts for one-third of safety-based withdrawn pharmaceuticals, making it the number one cause of drug withdrawal, limitation, and development termination. As of 2016, the Tufts Center for the Study of Drug Development estimates the cost of developing a new drug is on an average 2.89 billion US dollars. Because of this high cost, improved in vitro systems for predicting drug-induced toxicity are of great demand in the pharmaceutical industry to decrease late-stage drug attrition, advance rapid development, and reduce monetary loss.

Such predictive toxicity assays based on human pluripotent stem cells may aid in predicting potential safety issues of drug candidates early in its development process, provide information about the mechanisms of drug-induced organ toxicity, reduce the reliance on animal testing, and increase the relevance of preclinical safety tests. Human induced pluripotent stem cell (iPSC) differentiated cardiomyocytes are the ideal candidate for cardiotoxicity cell-based studies. They exhibit the molecular and functional properties of an intact human heart, and their electrical signatures can be monitored using non-destructive impedance sampling.

Interdigitated electrodes (IDEs), which are comprised of two individually addressable, interwoven, comb-like electrode structures, are one of the most favorable and widely used transducers as chemical and biological sensors because of their low cost, high sensitivity, and ease of fabrication. By affixing a culture well to the IDE substrate, a biosensor can be easily fabricated. This allows for cells to be cultured onto the surface and assessed with label-free electrical and optical assays. A low-voltage signal induces a current between the IDEs. The cells on the electrodes at the bottom of the culture well impede this current, and a change in impedance results. Measuring this impedance change across these electrodes gives an indirect measure of the number of cells in each culture well, as well as an assessment of the interaction between the cells and electrodes. Cellular impedance measurements are useful for studying cell growth and drug interactions in vitro without the use of destructive labelling procedures with fluorescent, chemiluminescent, or radioactive chemicals. Recently, these efforts are gaining industrial acceptance with efforts of collaboration between various tool vendors to introduce rapid assays with uniform standards for testing cardiotoxicity.

Conventional interdigitated electrodes (IDEs) used for impedance spectroscopy represent a label-free, non-invasive technique with a wide range of applications, including in vitro analysis of cells. Such IDEs have remained remarkably similar over the years with metal patterns defined on a silicon or a glass substrate on to which cells and materials are cultured for impedance analysis. Conventional IDEs suffer from undesired background noise.

Several IDE and impedance-based biosensors exist, but many of them require the use of expensive commercial systems for data analysis and involve cost prohibitive cleanroom-based fabrication approaches for the IDE micro and nanostructuring. These systems use very densely packed electrodes, which cover a majority of the substrate surface and prohibit optical tracking of cells. In addition, they tend to only measure cellular activity for hours, not days or weeks. Other approaches integrate microelectrode arrays with IDEs, which allows for more comprehensive measurement at the cost of more complex fabrication processes.

Typical methods for the fabrication of nanostructures include methods like photolithography, e-beam lithography, and focused ion beam lithography. These methods offer high quality nanostructures, but involve tedious procedures, long processing time, limited scalability, and high cost. To achieve scalability, bottom-up approaches like self-assembly have been used, but they are limited to select materials, and pattern versatility cannot be easily achieved using this approach. Sacrificial anodic aluminum oxide (AAO) templates for developing nanostructures are also widely used for fabricating nanostructures; however, the sacrificial nature of AAO and the required use of strong chemical etchants places a serious limitation on this method. Several unconventional lithographic methods have been developed to circumvent the limitations posed by conventional lithographic techniques. Among these techniques, nanoimprinting lithography (NIL) has attracted considerable attention. In NIL technique, many nanostructures can be replicated using an expensive NIL machine from a master mold. The feature size depends on the mold used to print the nanostructures. These nanostructures can subsequently be used as substrates for various applications, including interdigitated electrodes.

BRIEF SUMMARY

Various embodiments relate to interdigitated electrodes, such as nanostructured interdigitated electrodes (nIDEs) and plasmonic interdigitated electrodes (PIDEs). Plasmonic interdigitated electrodes, in particular, may combine the simplicity of an IDE with the sophistication of plasmonics for in vitro biosensing applications. Such PIDEs may separate the excitation source (light) from the detection signal (current), and thereby significantly reduce the undesired background noise, leading to higher sensitivity for bioanalysis compared with conventional IDEs. Various embodiments relate to methods of making plasmonic interdigitated electrodes, which allow the plasmonic substrate to be tuned not only to maximize the targeted interaction of the cells with the nanoscale geometry, but also for the excitation wavelength to minimize biological sample interference. In addition to being useful as cell-based biosensors, various embodiments may be used in the energy storage and distribution field as well. These and other features, aspects, and advantages of various embodiments will become better understood with reference to the following description, figures, and claims.

BRIEF DESCRIPTION OF THE FIGURES

Many aspects of this disclosure can be better understood with reference to the following figures, in which:

FIG. 25A: is an example according to various embodiments, illustrating calculated enhancement factor (EF) profiles of a nanohole array substrate at different cross-sections used for simulation of the plasmonic field concentration on the nanohole array substrate using Finite-Difference Time-Domain (FDTD) simulation software;

FIG. 25B: is an example according to various embodiments, illustrating schematic diagrams of the index profile of the simulated structure referenced with respect to FIG. 24A;

FIG. 25C: is an example according to various embodiments, illustrating an EF profile at the middle of a groove where two adjacent holes merge of a 164 nm nanohole array substrate as referenced with respect to FIG. 24A; and FIG. 25D: is an example according to various embodiments, illustrating an EF profile cut along x at z=32 nm of the 2D profile in FIG. 24C.

Figure 1:
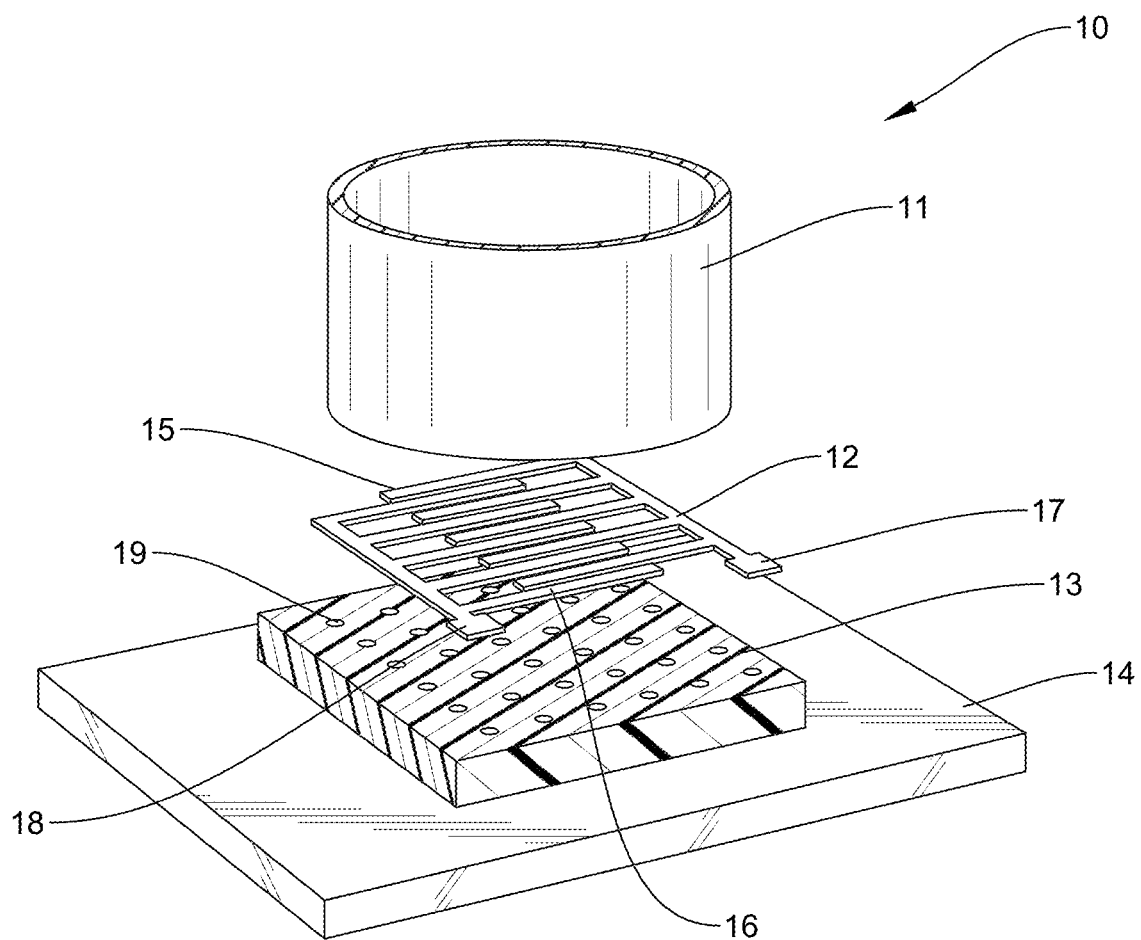
FIG. 1: is an example according to various embodiments, illustrating an exploded view of a plasmonic interdigitated electrode assembly.

The various embodiments are not limited to the examples illustrated in the figures.

DETAILED DESCRIPTION

Various embodiments may be understood more readily by reference to the following detailed description. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As used herein, the term "plasmonic" or "plasmonics" refers to the optical phenomena at the surfaces and interfaces of certain nanostructured materials, for example metals with dielectrics and semiconductors. This phenomena is the generation of an electric field (plasmonic field) due to the resonance between the electric field of incoming light and the electrons present on the surface of certain metals. In other words, it is the coherent oscillations of electrons with respect to the lattices. When nanostructures are used, this electric field can be localized and there can be plasmonic hot spots where the field is maximum. The sensing can be maximum at these hot spots. Plasmons are polar excitations: they are accompanied by the appearance of surface charges oscillating at optical frequencies. These oscillations cause the appearance of enhanced optical fields strongly localized at metal surfaces and interfaces. According to various embodiments a plasmonic field can be generated when a metal like gold is deposited on nanopatterns. Suitable metals may include but are not limited to one or more noble metals and combinations of noble metals, as well as semimetals, including but not limited to graphene, as well as combinations of various semimetals, and combinations of noble metals and semimetals. The metal may be, for example, gold or silver or a combination thereof.

As used herein, the term "impedance" generally refers to a measure of the opposition that a circuit presents to a current when a voltage is applied. For example, impedance may refer to the effective resistance of an electric circuit or component to alternating current, arising from the combined effects of ohmic resistance and reactance.

As used herein, the term "cardiomyocytes" refers to a cells that make up the cardiac muscle and may also be referred to as "myocardiocytes" or "cardiac myocytes."

As used herein, the term "plexitonic" refers to states associated with plexcitons, which are polaritonic modes that result from coherently coupled plasmons and excitons.

As used herein, the term "pitch" refers to a center-to-center distance between two structures or patterns. For example, a pitch of 200 nm would indicate a distance of 200 nm between the centers of two adjacent nanoholes.

As used herein, the term "standard temperature and pressure" generally refers to 20° C. to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C. Unless indicated otherwise all examples were conducted at standard temperature and pressure and all embodiments may be employed at standard temperature and pressure.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

According to various embodiments, it has been discovered that plasmonic effect may be utilized in combination with impedance for cell-based biosensors. The light absorption in metal films, nanoparticles, and nanostructures can be obtained by solving Maxwell's equations. Gustav Mie developed a theory to understand the light scattering and absorption of colloidal metal nanoparticles in 1908 by solving Maxwell's equation for a plane wave in spherical coordinate with a small sphere. By expanding the electromagnetic fields in an infinite series, scattering field and thereby extinction ($\sigma_{ext}$) and scattering cross section ($\sigma_{sca}$) can be determined. Therefore, the absorption cross-section $\sigma_{abs}$ can be given as shown in Equation (1):

$$\sigma_{ext} = \sigma_{sca} + \sigma_{abs} \quad (1).$$

When the electromagnetic field of the incoming light interacts with these structures, an induced charge separation called plasmonic effect takes place at the surface which is highly sensitive to the structural geometry, environmental factors and the angle of incidence of the electromagnetic radiation. Surface plasmonic resonance can take place when thin films are used and localized surface plasmonic resonance (LSPR) can occur when nanoparticles or nanostructures are used. For a given size of the nanostructures, the induced charge separation (plasmonic field) is maximum at certain frequency (resonance frequency) of the electromagnetic radiation. That is, the resonance occurs when the energy of electromagnetic radiation is the same as their free electron oscillation frequency. When metal nanoparticles are considered, the particle has the same frequency-dependent permittivity as the bulk metal. It is possible to approximate the metal permittivity from the Drude's model which assumes that conduction of electrons in metals can be considered as similar to molecules in the kinetic theory. According to this model, the electrons are free to move while the positive ionic core is immobile. The electrons scatter from the positive core and other electrons during their motion. The dielectric function of such conduction electrons changes as shown in Equation (2):

$$\varepsilon(\omega) = 1 - \frac{ne^2}{\varepsilon_0 m \omega^2}. \quad (2)$$

where $\varepsilon(\omega)$ is the dielectric constant at an angular frequency of the exciting radiation, $\omega$; n is the electron density; $\varepsilon_0$ is the vacuum permittivity; e and m are charge and mass of the electron respectively. It can be seen from Equation (2) that the collective oscillations of the plasmonic electrons are dependent on the dielectric constant of the structures. Analytical solutions for particles with other geometries can also be derived by expanding the Mie theory. Numerical techniques like Finite-Difference Time-Domain (FDTD) may also be used to solve Maxwell's equations.

The surface plasmon property of some materials may be utilized for making optical biosensors because: (i) the plasmonic wavelength is dependent on the refractive index (in effect the dielectric constant), binding of analyte can be detected by the shift in the plasmonic extinction peak; and (ii) as a result of the large electromagnetic field, highly enhanced optical/physical phenomena like fluorescence and Raman scattering can be used to detect an analyte. Various embodiments are based on a hypothesis that electrochemical impedance of the analyte applied on the plasmonic substrate can be considerably altered due to the change in the dielectric constant, electronic charge transport, and heating effect due to Mie scattering at the plasmonic resonance frequency. The plasmonic field generated when the nanostructures, according to various embodiments, are illuminated with a very low intensity laser beam (for example a laser pointer) is maximum when excited at its resonance peak. Impedance will be increased because of the highly dispersive charge transport through the electrode/substrate. LSPR is highly localized and, therefore, the sensitivity (or fidelity) of this technique will be high compared to other techniques like MEAs and IDEs without plasmonics. In addition, localized heating due to Mie scattering can increase the temperature of the medium thereby increasing the impedance.

For sensing applications, the notions of hybridized states exhibiting Fano resonance and Rabi-splitting have been demonstrated to significantly enhance the sensitivity of molecular detections. These are proposed to be promising directions for attaining a few molecule-level detections. Various embodiments provide improved scalability and practicability of developing low cost plasmonic substrates. Various embodiments combine the simplicity of impedance-based microelectrodes and the novelty of plexitonic effect of plasmonic nanostructures with the goal of achieving non-invasive and non-contact single cell analysis where cardiotoxicity is used as a test vehicle. This is based on the principle that when the plasmonic substrate is tuned to the electronic absorption maximum of a dye (for example dye labeled analyte), a hybridized energy state of plasmons and excitons can be generated. Such a hybridized energy state can exhibit Rabi splitting as well as highly enhanced Raman and fluorescence signals of the analyte. This enhancement of signals can result in the single cell detection of dye labelled analyte. Techniques for tuning plasmonic substrates are described later.

Various embodiments provide a nanostructured tool that can revolutionize the detection of optical and electrical signals from a single cell and a network of cardiac cells. As a result, various embodiments will be vital to several in vitro biosensing applications such as studying cellular morphology, proliferation, and quantification enabling the ability for the first time to study molecular interactions in cells without the need for invasive technologies. In addition to providing a nanostructured device, such as a plasmonic interdigitated electrode, various embodiments provide innovations in the field of biophotonics and plasmonics by introducing optimized printed plasmonic nanostructures that can be fabricated in the matter of minutes. Key innovations in rapid structuring of shadow masks with potentially nano-scale feature sizes for high specificity and selectivity will be developed outside the cleanroom. Lastly, new cardiotoxicity models as test vehicles with potential for both single cell and network level analysis of drug compounds with these revolutionary PIDEs have been developed.

Various embodiments relate to methods of rapid nanofabrication of nanostructured interdigitated electrodes (nIDEs) for long-term in vitro analysis of human-induced pluripotent stem cell differentiated cardiomyocytes. Various embodiments relate to the development of IDEs patterned onto nanostructured PAN substrates using rapid micro/nanofabrication technologies. The resulting nanostructured IDEs (or nIDEs) demonstrated excellent biocompatibility of 40,000 RFU with low standard deviation with respect to iCell$^2$ cardiomyocytes. The nIDEs were developed as a tool for rapid screening of toxins with an impedance metric and they demonstrated an impedance (110.19 kΩ at 1 kHz for DIV10 and 243.21 kΩ at 1 kHz for DIV18) that was higher than the IDEs with just an aqueous medium (27.37 kΩ at 1 kHz) which was used as a control. In addition, the nIDEs with cells showed increased impedance as evidenced by a Cell Index (CI) increase from 0 to 8 with increasing days in vitro of cell culturing. This result is as predicted because impedance should increase as cell coverage increases because of the cell-electrode interaction. Long term cell culture (DIV18) was demonstrated with iCell Cardiomyocytes, and most significantly, a 100× improvement in device performance when fabricated on nanostructured substrates was demonstrated with cellular index calculations. Various embodiments described herein are the first to report this result with devices of interelectrode spacing or pitch of 1 mm over a period of 18 days with human cardiomyocytes.

Devices according to various embodiments can be about 100 times larger than available commercial systems, including a commercial system with 10 μm pitch IDEs on a glass substrate fabricated with a complex photolithographic technique, involving several steps. Unexpectedly, even though devices according to various embodiments are about 100 times larger, they provide similar CI increases from cell growth (CI=1.1 on DIV10 increasing to CI equal to approximately 7-8 on DIV17). Without wishing to be bound by theory, it is believed that the comparable performance is due to the nanoscale structure patterned onto the substrate of the pIDEs. As a result, the pIDE shows an increased sensitivity compared to commercial IDE systems, which have an electrode gap that is 100 times smaller. This increase in sensitivity may be due to the increased electrode surface area provided by the nanoholes. When surface area increases, capacitance increases; thus, impedance decreases, giving greater sensitivity. Finally, the cardiotoxicity testing utility of our devices were successfully demonstrated with the expected response of decreased cellular index from 2.34 to 1.13 in response to increased concentrations of a model drug, norepinephrine.

Adverse cardiac events are a major cause of late-stage drug development withdrawals. Improved in vitro systems for predicting cardiotoxicity are of great interest to prevent these events and to reduce the expenses involved in the introduction of cardiac drugs into the marketplace. Interdigitated electrodes (IDEs) affixed with a culture well provide a simple, suitable solution for in vitro analysis of cells because of their high sensitivity, ease of fabrication, and label-free, non-destructive analysis. Culturing human pluripotent stem cell differentiated cardiomyocytes onto these IDEs allows for the use of the IDE-cell combination in predictive toxicity assays. IDEs with smaller interdigitated distances allow for greater sensitivity, but typically require cleanroom fabrication.

Various embodiments provide a simple IDE geometry on a printed nanostructured substrate, demonstrating a Cellular Index (CI) increase from 0 to 7.7 for human cardiomyocytes, and a decrease in CI from 2.3 to 1 with increased concentration of the model drug, norepinephrine. The nanostructuring results in a 100× increased sensitivity of the 1 mm pitch IDEs, according to various embodiments, when compared to traditional IDEs with a pitch of 10 μm. Moreover, the entire nanostructured IDE (nIDE) or the entire plasmonic IDE (pIDE) may be fabricated and assembled in a rapid nanofabrication environment, thus allowing for rapid design changes and robust fabrication of devices.

Various embodiments provide an impedance-based sensor that allows for longer term in vitro cellular analysis with high-fidelity. In this context the term "high-fidelity" refers to a sensor that can detect even a single cell or a very small number of cells. According to various embodiments, a high-fidelity interdigitated electrode sensor or device can detect a single cell to a cluster of about 1 million cells or more.

According to various embodiments, interdigitated electrodes may be placed on a nanostructured polymer substrate, such as a nanostructured polyacrylonitrile (PAN) substrate, whose geometry is designed to maximize the interaction with the electrodes and cells. As discussed above, an increase in sensitivity may be provided, according to various embodiments, due to the increased electrode surface area provided by the nanoholes. When surface area increases, capacitance increases; thus, impedance decreases, giving greater sensitivity. By adjusting the geometry of the polymer layer and thereby the plasmonic structure, the plasmonic interaction can be maximized at places (hot spots) where the cells are present. As a result, the device is fashioned as nanostructured Interdigitated Electrodes (nIDEs). Both the IDE and the nanostructured PAN substrate are fabricated utilizing "Rapid Micro/Nanofabrication Approaches" in the benchtop. This results in cost effectiveness, rapid translation from design to a fabricated part, utilization of direct write techniques, and the ability to reduce drug candidate testing times by an order of magnitude or more with dramatically increased sensitivity. For example, according to various embodiments, it is possible to go from design to a device in a single step. In this case, the nanostructured substrate may be 3-D printed and electrodes may be deposited in one step. The interaction of the nanostructured plasmonic substrate with the electrodes should increase the sensitivity of the IDEs, and as a result, electrodes with a larger pitch should have the same performance as electrodes that are orders of magnitude smaller. In addition, various embodiments demonstrate the utility of the nIDE for cardiotoxicity screening with varying concentrations of a model drug.

FIG. 1 is an example according to various embodiments, illustrating an exploded view of a plasmonic interdigitated electrode assembly 10, having a culture well 11, an interdigitated electrode pattern 12, a nanostructured polymer layer 13 (which may also be referred to as a nanoscale plasmonic substrate), and a substrate 14. FIG. 1 shows these structures in an exploded view so that each structure may be seen, but once assembled, the nanostructured polymer layer 13 may rest upon or be affixed to the substrate 14; the interdigitated electrode pattern 12 may rest upon or be affixed to the nanostructured polymer layer 13; and the culture well 11 may rest upon or be affixed to the interdigitated electrode pattern 12 and/or the nanostructured polymer layer 13 and/or the substrate 14. The plasmonic interdigitated electrode assembly 10 may be employed as an impedance sensing platform and may be useful as a tool to non-invasively monitor cells in vitro with the potential capability for single cell analysis and high sensitivity.

The fully assembled plasmonic interdigitated electrode assembly 10 may have any suitable size. For example, the fully assembled plasmonic interdigitated electrode assembly 10 may have a length within a range having a lower limit and/or an upper limit. The range may include or exclude the lower limit and/or the upper limit. The lower limit and/or upper limit can be selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mm. For example, according to certain embodiments, the fully assembled plasmonic interdigitated electrode assembly 10 may have a length of about 10 mm, or any combination of lower limits and upper limits described. The fully assembled plasmonic interdigitated electrode assembly 10 may have a width within a range having a lower limit and/or an upper limit. The range may include or exclude the lower limit and/or the upper limit. The lower limit and/or upper limit can be selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mm. For example, according to certain embodiments, the fully assembled plasmonic interdigitated electrode assembly 10 may have a width of about 10 mm, or any combination of lower limits and upper limits described.

Still referring to FIG. 1, the culture well 11 may be 3-D printed from any suitable resin material such as thermoplastic polymers and photodefinable polymers. The culture well 11 may be dip-coated with a biocompatible polymer, such as polydimethylsiloxane (PDMS), Poly Methyl Methacrylate (PMMA), Polystyrene (PS), and others known to those skilled in the art. The biocompatibility arises from the need to have the materials emanate no toxins or leachants when in contact with cells. The biocompatible polymer may cover the culture well 11 in part or in its entirety to improve biocompatibility of the printed resin material. The culture well 11 may be attached to the substrate 14 and/or to the nanostructured polymer layer 13 and/or to the electrode pattern 12 using a biocompatible epoxy.

The biocompatible polymer coating may have a thickness within a range having a lower limit and/or an upper limit. The range may include or exclude the lower limit and/or the upper limit. The lower limit and/or upper limit can be selected from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, and 150 µm. For example, according to certain embodiments, the biocompatible polymer coating may have a thickness of from about 1 to about 100 µm, or any combination of lower limits and upper limits described.

The culture well 11 may have any suitable dimensions. For example, the culture well 11 may have an inner diameter within a range having a lower limit and/or an upper limit. The range may include or exclude the lower limit and/or the upper limit. The lower limit and/or upper limit can be selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mm. For example, according to certain embodiments, the culture well 11 may have an inner diameter of about 10 mm, or any combination of lower limits and upper limits described. The culture well 11 may have a height within a range having a lower limit and/or an upper limit. The range may include or exclude the lower limit and/or the upper limit. The lower limit and/or upper limit can be selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mm. For example, according to certain embodiments, the culture well 11 may have a height of about 10 mm, or any combination of lower limits and upper limits described.

Still referring to FIG. 1, the interdigitated electrode pattern 12 may comprise any suitable metal, preferably a good plasmonic metal on which surface plasmons may be well-pronounced as resonances. Suitable metals may include but are not limited to one or more noble metals and combinations of noble metals, as well as semimetals, including but not limited to graphene, as well as combinations of various semimetals, and combinations of noble metals and semimetals. The metal may be, for example, gold or silver or a combination thereof. The interdigitated electrode pattern 12 may include one or more first fingers 15 and one or more second fingers 16. As shown in FIG. 1, the one or more first fingers 15 may be interdigitated with the one or more second fingers 16, such that the one or more first fingers 15 and the one or more second fingers 16 are interlaced but not touching. The interdigitated electrode pattern 12 may further include a first contact pad 17 and a second contact pad 18 to which lead wires (not shown in FIG. 1, see FIG. 11) may be connected. The interdigitated electrode pattern 12 may be any suitable dimension.

The interdigitated electrode pattern 12 may have a width within a range having a lower limit and/or an upper limit. The range may include or exclude the lower limit and/or the upper limit. The lower limit and/or upper limit can be selected from about 1, 5, 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, and 1500 µm. For example, according to certain embodiments, the interdigitated electrode pattern 12 may have a width of about 800 µm, or any combination of lower limits and upper limits described.

The interdigitated electrode pattern 12 may have a length within a range having a lower limit and/or an upper limit. The range may include or exclude the lower limit and/or the upper limit. The lower limit and/or upper limit can be selected from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, and 10 mm. For example, according to certain embodiments, the interdigitated electrode pattern 12 may have a length of about 1 mm, or any combination of lower limits and upper limits described.

The interdigitated electrode pattern 12 may have a pitch, defining a distance between two adjacent electrode fingers. The pitch may define the center-to-center distance between the two electrode fingers. The pitch may also be measured as an edge-to-edge distance, provided that the distance is measured orthogonally relative to the edge, for example a measurement of a top-edge-to-top-edge distance between two adjacent electrode fingers or a bottom-edge-to-bottom-edge distance between two adjacent electrode fingers. For purposes of the following ranges, the pitch of the interdigitated electrode pattern 12 defines the center-to-center distance between the two electrode fingers. The pitch may be within a range having a lower limit and/or an upper limit. The range may include or exclude the lower limit and/or the upper limit. The lower limit and/or upper limit can be selected from about 0.0005, 0.001, 0.005, 0.01, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, and 10 mm. For example, according to certain embodiments, the interdigitated electrode pattern 12 may have a pitch of about 1 mm, or any combination of lower limits and upper limits described.

The interdigitated electrode pattern 12 may have a thickness within a range having a lower limit and/or an upper limit. The range may include or exclude the lower limit and/or the upper limit. The lower limit and/or upper limit can be selected from about 5, 10, 15, 20, 25, 30, 35, 40, 45, 50, 55, 60, 65, 70, 75, 80, 85, 90, 95, and 100 nm. For example, according to certain embodiments, the interdigitated electrode pattern 12 may have a thickness of about 30 nm, or any combination of lower limits and upper limits described.

Still referring to FIG. 1, the nanostructured polymer layer 13 may include a plurality of nanoholes 19. The plurality of nanoholes may be arranged in a regular pattern. Each of the plurality of nanoholes 19 may extend entirely or partially through the thickness of the nanostructured polymer layer 13. Without wishing to be bound by theory, it is believed that at least a majority of the nanoholes must extend through the entire thickness of the nanostructured polymer layer in order to provide a suitable plasmonic effect.

Still referring to FIG. 1, the nanostructured polymer layer 13 may comprise any synthetic or natural polymer or copolymer or blend or combination thereof. For example, the nanostructured polymer layer may comprise polyacrylonitrile (PAN), polystyrene, polymethylmethacrylate (PMMA), polycarbonate, low-density polyethylene (LDPE), high-density polyethylene (HDPE), polypropylene (PP), polyvinyl chloride (PVC), and combinations thereof. Again, the nanostructured polymer layer 13 may also be referred to as a nanoscale plasmonic substrate. The nanoscale geometry of the nanoscale plasmonic layer may be tuned to maximize the targeted interaction of this layer with electrodes and cells which is subsequently measured. Tuning the nanoscale geometry of the nanostructured polymer layer 13 may include varying its length, width, thickness, and pitch, as well as varying the number, size (or diameter), and array layout of the nanoholes 19. The array layout of the nanoholes refers to the pattern in which the nanoholes are arranged. For example, the nanoholes may be arranged in square or hexagonal pattern. The grid pattern may position the nanoholes in a square alignment or offset relative to each other.

The nanoholes 19 may have a pitch within a range having a lower limit and/or an upper limit. The range may include or exclude the lower limit and/or the upper limit. The lower limit and/or upper limit can be selected from about 10, 50, 100, 150, 200, 250, 300, 350, 400, 450, 500, 550, 600, 650, 700, 750, 800, 850, 900, 950, and 1000 nm. For example, according to certain embodiments, the nanoholes may have a pitch of from about 50 to about 500 nm, or any combination of lower limits and upper limits described. The pitch, in this context, being a center-to-center distance between adjacent nanoholes, also indicates the number of holes per unit area. Tuning the nanoscale geometry of the nanostructured polymer layer 13 to maximize the targeted interaction of this layer with electrodes and cells may be beneficial, because such an interaction could dramatically improve the sensitivity of interdigitated electrodes, enabling the plasmonic interdigitated electrodes, according to various embodiments, to be a useful tool for the electrical and optical analysis of single cells and a network of cells. Methods for tuning the size of the nanoholes are described later. As used herein, the phrase "the nanoholes 19 may have a pitch" is synonymous with the phrase "the nanostructured polymer layer 13 may have a pitch." The "pitch" of the polymer layer 13 refers to the center-to-center distance between nanoholes 19.

Each of the plurality of nanoholes 19 may have a size or a diameter within a range having a lower limit and/or an upper limit. The range may include or exclude the lower limit and/or the upper limit. The lower limit and/or upper limit can be selected from about 10, 20, 30, 40, 50, 75, 100, 125, 150, 175, 200, 225, 250, 275, 300, 325, 350, 375, 400, 425, 450, 475, and 500 nm. For example, according to certain embodiments, each of the plurality of nanoholes 19 may have a size or a diameter in a range of from about 30 nm to about 400 nm, or any combination of lower limits and upper limits described. The size or diameters listed above may be uniform, meaning that all of the nanoholes have approximately the same size or diameter. The sizes or diameters listed above may be nonuniform, meaning that each nanohole may have a size or diameter that is independently selected from the ranges described. The sizes or diameters listed above may also indicate averages, meaning that the average size or diameter of all nanoholes in the nanostructured polymer layer 13 is within the particular range.

The nanostructured polymer layer 13 may have a length within a range having a lower limit and/or an upper limit. The range may include or exclude the lower limit and/or the upper limit. The lower limit and/or upper limit can be selected from about 1, 1.5, 2, 2.5, 3, 3.5, 4, 4.5, 5, 5.5, 6, 6.5, 7, 7.5, 8, 8.5, 9, 9.5, and 10 mm. For example, according to certain embodiments, the nanostructured polymer layer 13 may have a length of about 5 mm, or any combination of lower limits and upper limits described.

The nanostructured polymer layer 13 may have a width within a range having a lower limit and/or an upper limit. The range may include or exclude the lower limit and/or the upper limit. The lower limit and/or upper limit can be selected from about 1, 1.5, 2, 2.5, 3, 3.5, 4, 4.5, 5, 5.5, 6, 6.5, 7, 7.5, 8, 8.5, 9, 9.5, and 10 mm. For example, according to certain embodiments, the nanostructured polymer layer 13 may have a width of about 5 mm, or any combination of lower limits and upper limits described. The nanostructured polymer layer 13 may have a thickness within a range having a lower limit and/or an upper limit. The range may include or exclude the lower limit and/or the upper limit. The lower limit and/or upper limit can be selected from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, and 20 µm. For example, according to certain embodiments, the nanostructured polymer layer 13 may have a thickness of about 10 µm, or any combination of lower limits and upper limits described.

Still referring to FIG. 1, the substrate 14 may comprise any suitable glass, such as, for example, a borosilicate glass. The glass may have any suitable dimensions.

A coating may be applied to one or more portions of the electrode assembly 10, including to the culture well 11, to the interdigitated electrode pattern 12, to the nanostructured polymer layer 13, and/or optionally to the substrate 14. The coating may be a suitable biocompatible coating to facilitate attachment of cells. According to various embodiments the coating may be fibronectin.

Figure 2:
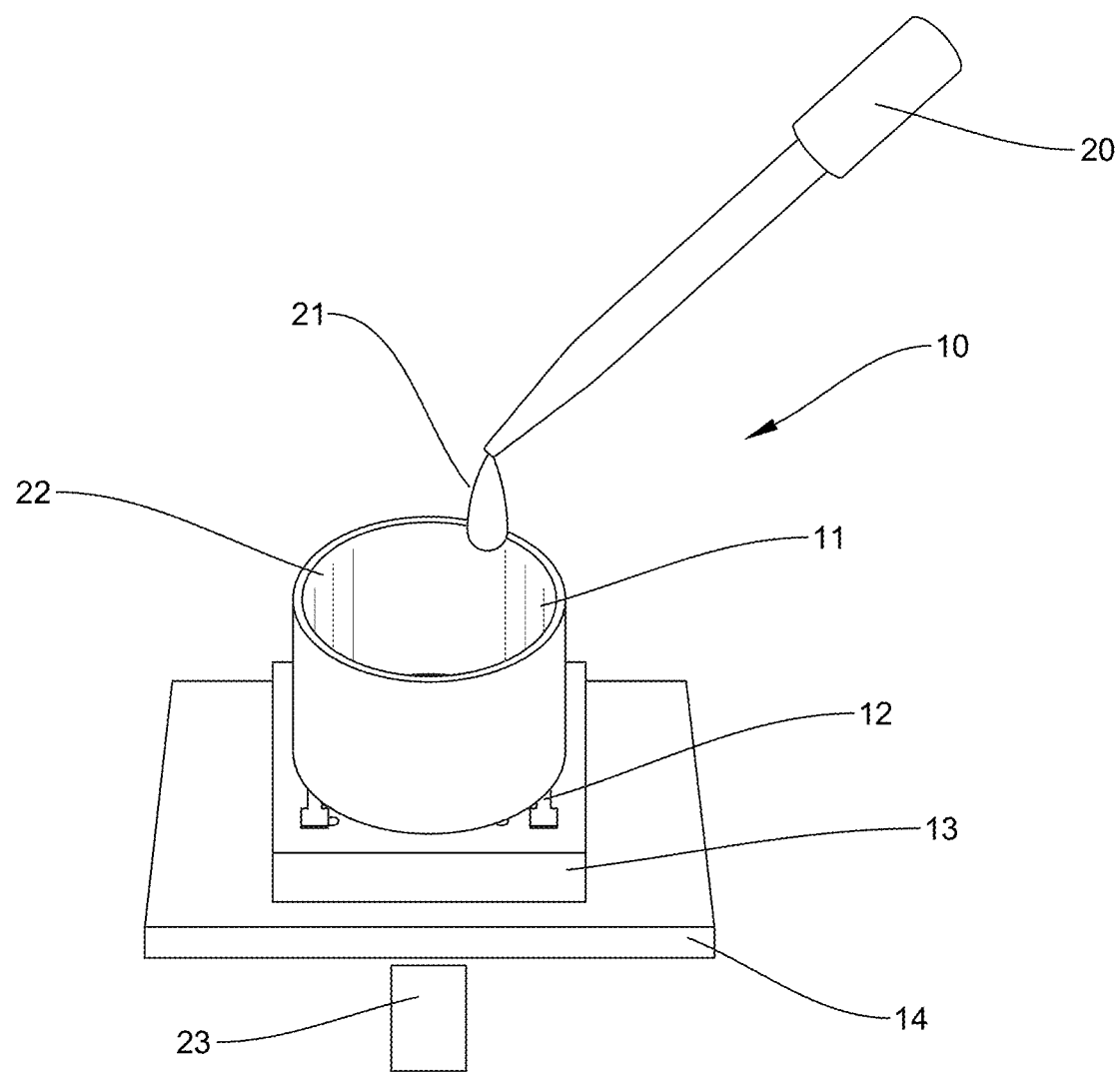
FIG. 2: is an example according to various embodiments, illustrating a schematic view of a plasmonic interdigitated electrode assembly.

FIG. 2 is an example according to various embodiments, illustrating a schematic view of a plasmonic interdigitated electrode assembly. As shown in FIG. 2, a delivery device, such as a pipette 20, may be used to add culture material 21 to inner cavity 22 of the culture well 11. A light source 23, such as a laser, may direct light or a laser beam through the glass substrate, which may be transparent. The light may then interact with the nanostructured polymer layer 13 and/or the interdigitated electrode pattern 12 to produce a plasmonic effect. For example, surface plasmons, may be exited on the surface of the interdigitated electrode pattern 12. The surface plasmons may be coherent collective oscillations of electrons between the first plurality of fingers 15 and the second plurality of fingers 16, which are interdigitated. The interdigitated electrode pattern 12 may also include a first contact pad 17 and a second contact pad 18 to which lead wires may be connected. The plasmonic interdigitated electrode assembly may then be used as impedance sensing platforms to non-invasively monitor cells in vitro, that are contained within the culture well 11 and in contact with the interdigitated electrode pattern 12. Different concentrations of cells in the culture well 11, causing different impedances. The impedance sensing platforms, according to various embodiments may measure the frequency-dependent alterations of passive electrical properties of networks of cells.

FIGS. 3A, 3B, 3C, and 3D, together, illustrate a method 30 of preparing the nanostructured polymer layer 13 and securing it to the substrate 14. Unlike prior methods, the methods according to various embodiments are very economical. Prior localized surface plasmonic resonance (LSPR) substrates were fabricated using expensive techniques such as Electron Beam Lithography (EBL) and Focused Ion Beam Lithography (FIBL). These techniques are very time consuming and labor intensive and making a large number of substrates to use in real-world applications is almost impossible. FIG. 3A is an example according to various embodiments, illustrating a silicon mold 31 having a plurality of nanopillars 32, which may be used in the method 30 of making the nanostructured polymer layer 13, having a plurality of nanoholes 19. FIG. 3B is an example according to various embodiments, illustrating a polymer spin-coated 33 onto the silicon mold 31 of FIG. 3A to form polymer film 34. The polymer film 34 may then be cured at a temperature within a range having a lower limit and/or an upper limit. The range may include or exclude the lower limit and/or the upper limit. The lower limit and/or upper limit can be selected from about 120, 125, 130, 135, 140, 145, 150, 155, 160, 165, and 170° C. For example, according to certain embodiments, the polymer film 34 may then be cured at a temperature in a range of from about 120° C. to about 170° C., or at about 150° C., or any combination of lower limits and upper limits described.

FIG. 3C is an example according to various embodiments, illustrating that after being cured, polymer film 34, having a plurality of nanoholes 19, may be peeled from the silicon mold 31 of FIGS. 3A and 3B to form the nanostructured polymer layer 13. FIG. 3D is an example according to various embodiments, illustrating the nanostructured polymer layer 13 of FIG. 3C after being transferred to a glass substrate 14. The polymer layer 13 may then optionally be etched with $O_2$ plasma with different durations. For example, using a plasma etching machine in the presence of oxygen gas. Etching is one way to tune the size of the nanoholes. According to various embodiments, tuning the plasmonic nanostructures may include optionally optimizing the nanohole size using a simple and inexpensive plasma etching process using any commonly available plasma cleaner. Suitable plasma cleaners may include but are not limited to Plasma Etch Plasma Cleaner, Plasma Therm Reactive Ion Etcher, STS Reactive Ion Etcher.

Figure 4:
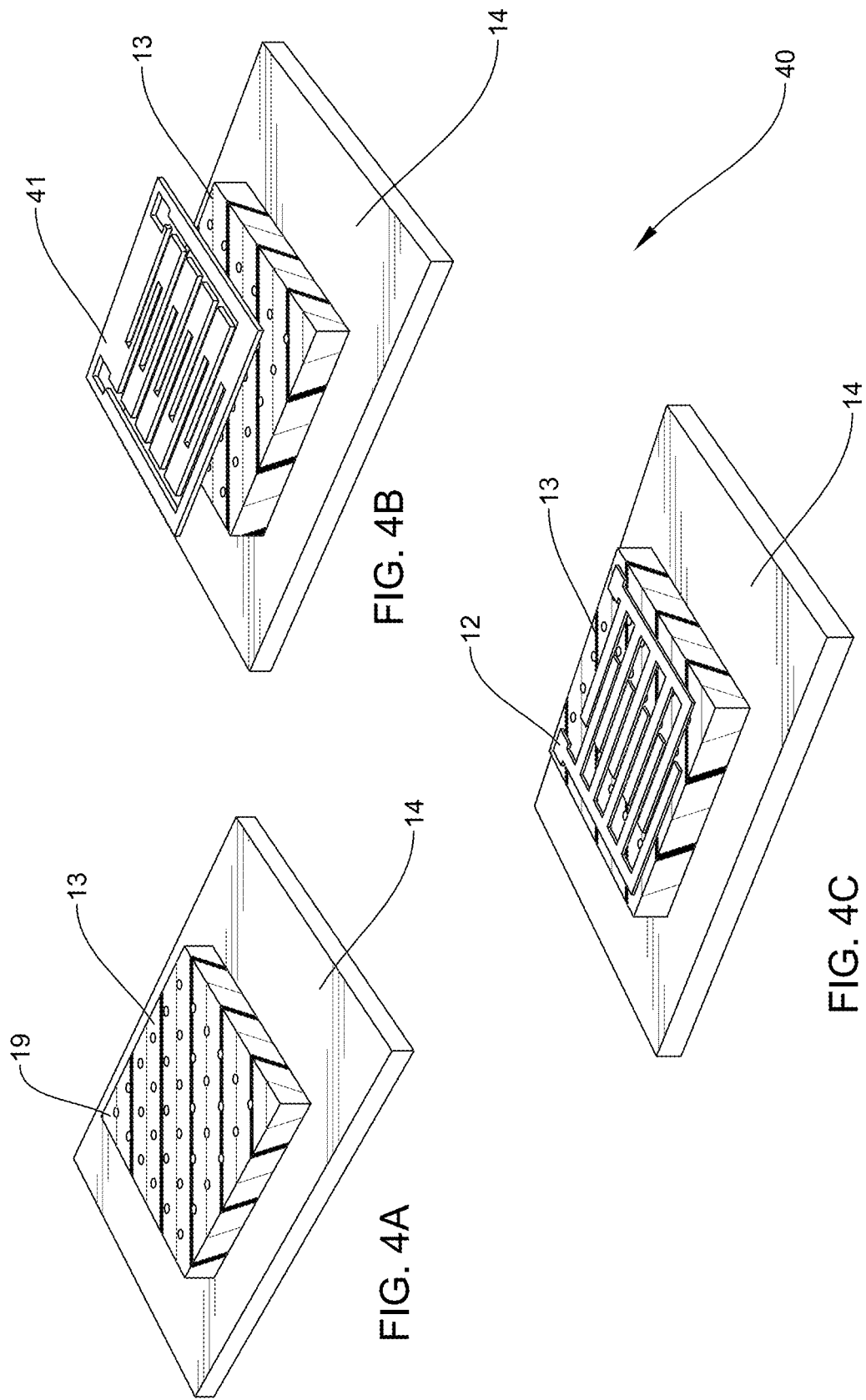
FIG. 4A: is an example according to various embodiments, illustrating a polymeric film having a plurality of nanoholes disposed on a glass substrate.
FIG. 4B: is an example according to various embodiments, illustrating a micromachined shadow mask disposed on the polymeric film of FIG. 4A.
FIG. 4C: is an example according to various embodiments, illustrating a pattern of metal, such as gold, that has been deposited on the polymeric film of FIG. 4A in the interdigitated pattern provided by the micromachined shadow mask of FIG. 4B.

FIGS. 4A, 4B, and 4C, together illustrate a method 40 of depositing an interdigitated electrode pattern 12 onto a nanostructured polymer layer 13. FIG. 4A is an example according to various embodiments, illustrating a nanostructured polymer layer 13 having a plurality of nanoholes disposed on a glass substrate 14. FIG. 4B is an example according to various embodiments, illustrating a micromachined shadow mask 41 disposed on the nanostructured polymer layer 13 of FIG. 4A. FIG. 4C is an example according to various embodiments, illustrating a pattern of metal, such as gold, that has been deposited on the nanostructured polymer layer 13 of FIG. 4A in an interdigitated electrode pattern 12 provided by the micromachined shadow mask of FIG. 4B.

Figure 5:
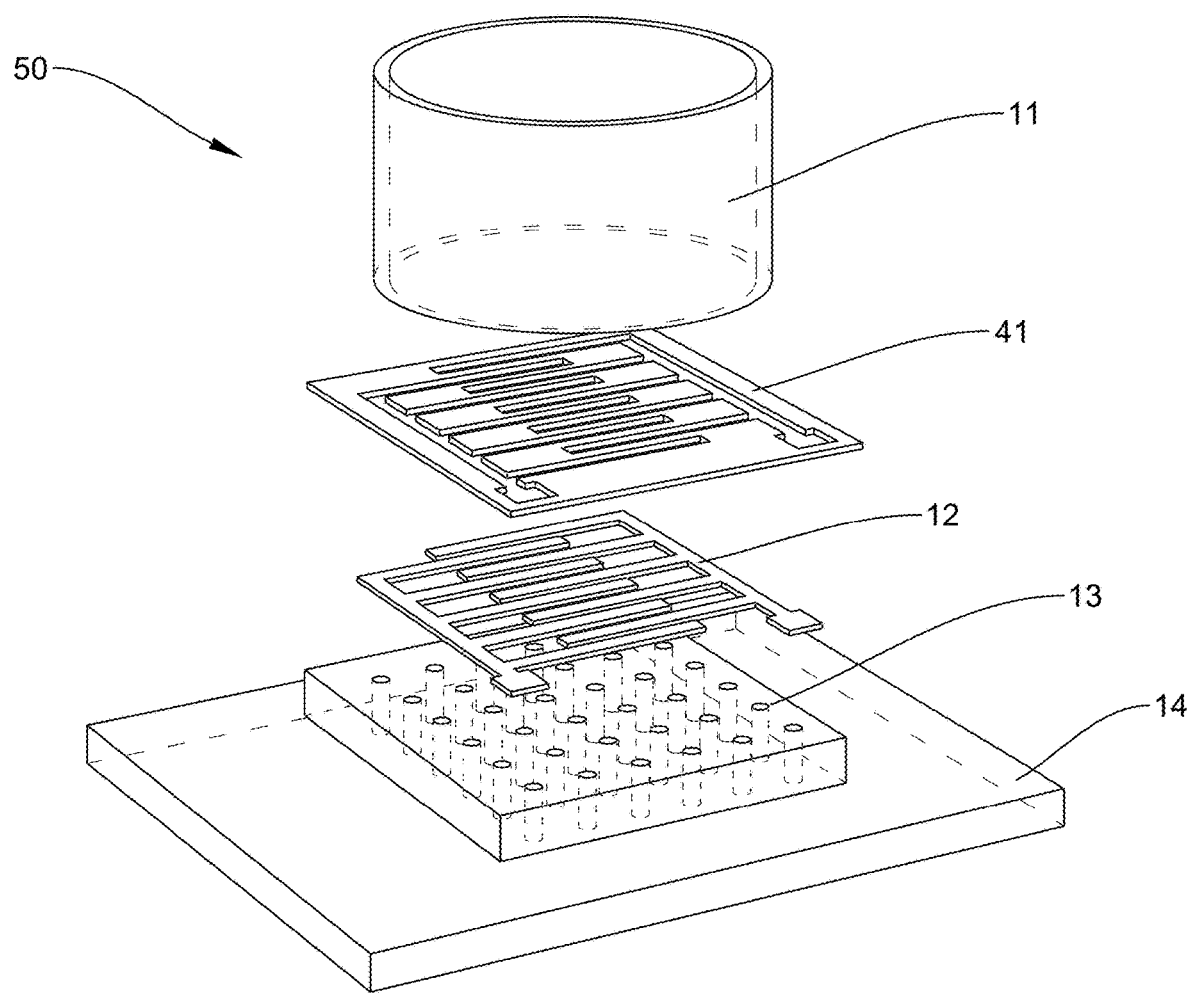
FIG. 5: is an example according to various embodiments, illustrating an exploded view of a plasmonic interdigitated electrode assembly with a micromachined shadow mask (to be removed prior to final assembly)

FIG. 5 is an example according to various embodiments, illustrating an exploded view of a plasmonic interdigitated electrode assembly 50 with a micromachined shadow mask 41 (which may optionally be removed prior to final assembly). The mask may be constructed out of any suitable material, such as stainless steel, in this case. The mask may also be constructed from aluminum, copper, nickel, polymeric materials, and combinations thereof. Exemplary polymeric materials include but are not limited to poly-oxydiphenylene-pyromellitimide (also known as, Kapton), poly (methyl methacrylate) (PMMA), polyethylene terephthalate (PET), polyethylene naphthalate (PEN), and combinations thereof. Like the plasmonic interdigitated electrode assembly 10, shown in FIG. 1, the plasmonic interdigitated electrode assembly 50 also includes a culture well 11, an interdigitated electrode pattern 12, a nanostructured polymer layer 13, and a substrate 14.

EXAMPLES

The following examples are put forth to provide those of ordinary skill in the art with a complete disclosure and description of how to perform the methods and use the devices disclosed and claimed herein. Efforts have been made to ensure accuracy with respect to numbers (e.g., amounts, temperature, etc.), but some errors and deviations should be accounted for. The purpose of the following examples is not to limit the scope of the various embodiments, but merely to provide examples illustrating specific embodiments.

Figure 12:
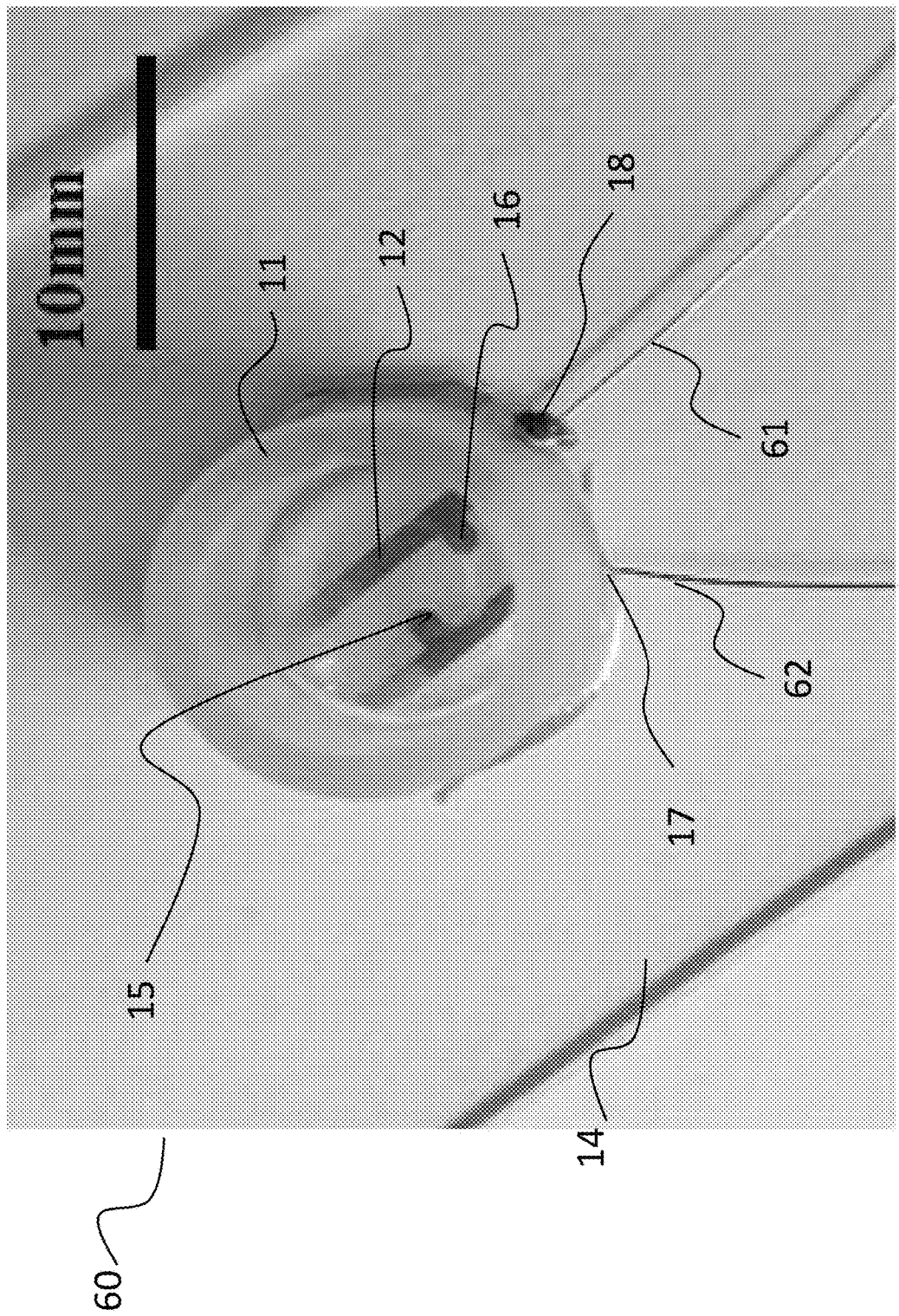
FIG. 12: is an example according to various embodiments, showing a photograph of a plasmonic interdigitated electrode assembly.

A number of plasmonic interdigitated electrode assemblies were prepared. FIG. 12 is an example according to various embodiments, showing a photograph of a plasmonic interdigitated electrode assembly 60. The plasmonic interdigitated electrode assembly 60, has a culture well 11, an interdigitated electrode pattern 12, a nanostructured polymer layer of PolyAcryloNitrile (not visible), and a glass substrate 14. The interdigitated electrode pattern 12 included a first finger 15 and a second finger 16, which are interdigited. The interdigitated electrode pattern 12 also included a first contact pad 17 and a second contact pad 18 to which lead wires 61, 62 were connected. The plasmonic interdigitated electrode assembly 60 and others like it were employed, in the following examples, as impedance sensing platforms to non-invasively monitor cells in vitro.

Figure 6:
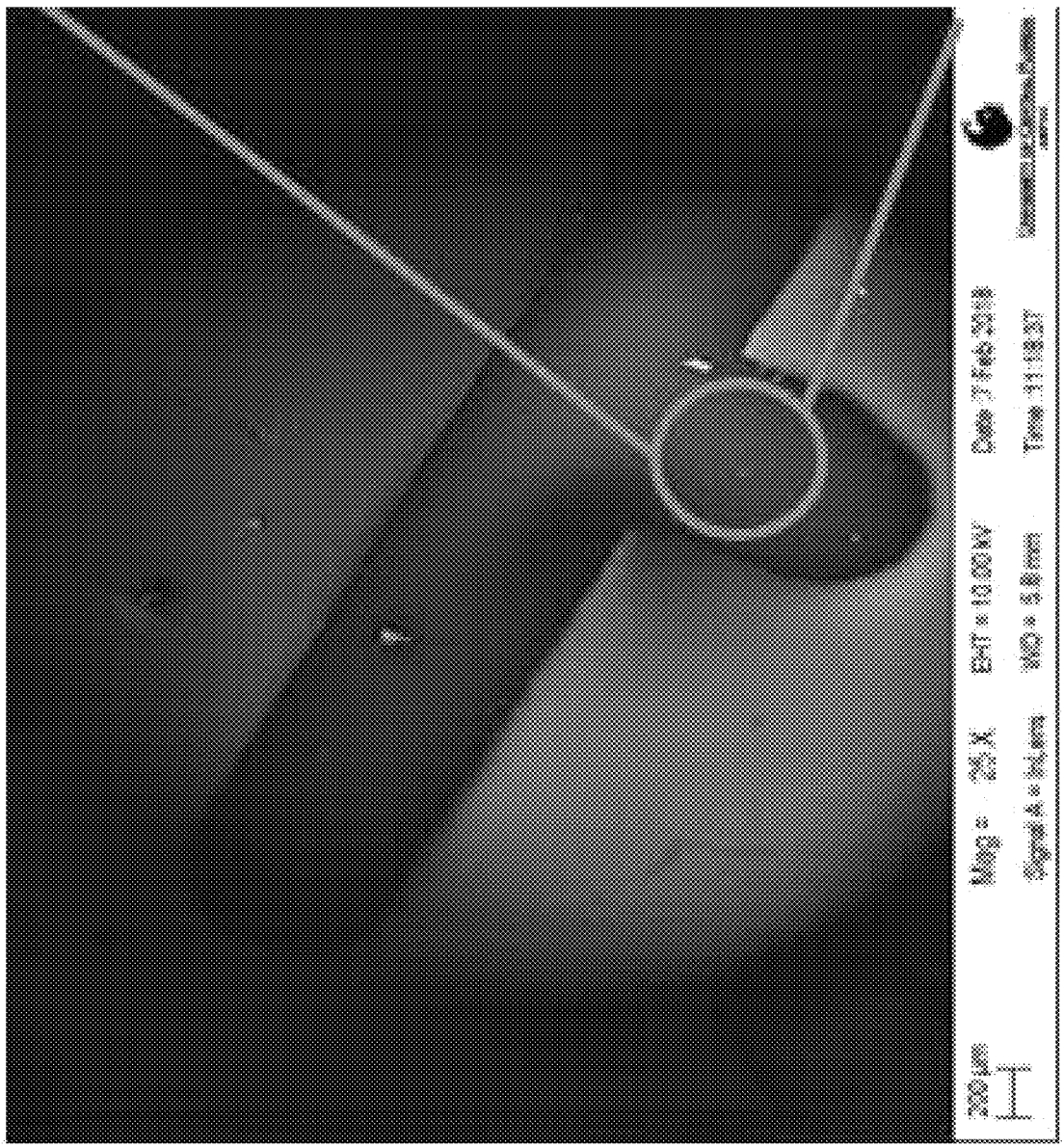
FIG. 6: is an example according to various embodiments, illustrating a scanning electron microscope (SEM) image of a finger of an interdigitated electrode deposited on a nanostructured polymer layer of PolyAcryloNitrile (PAN)
Figure 7:
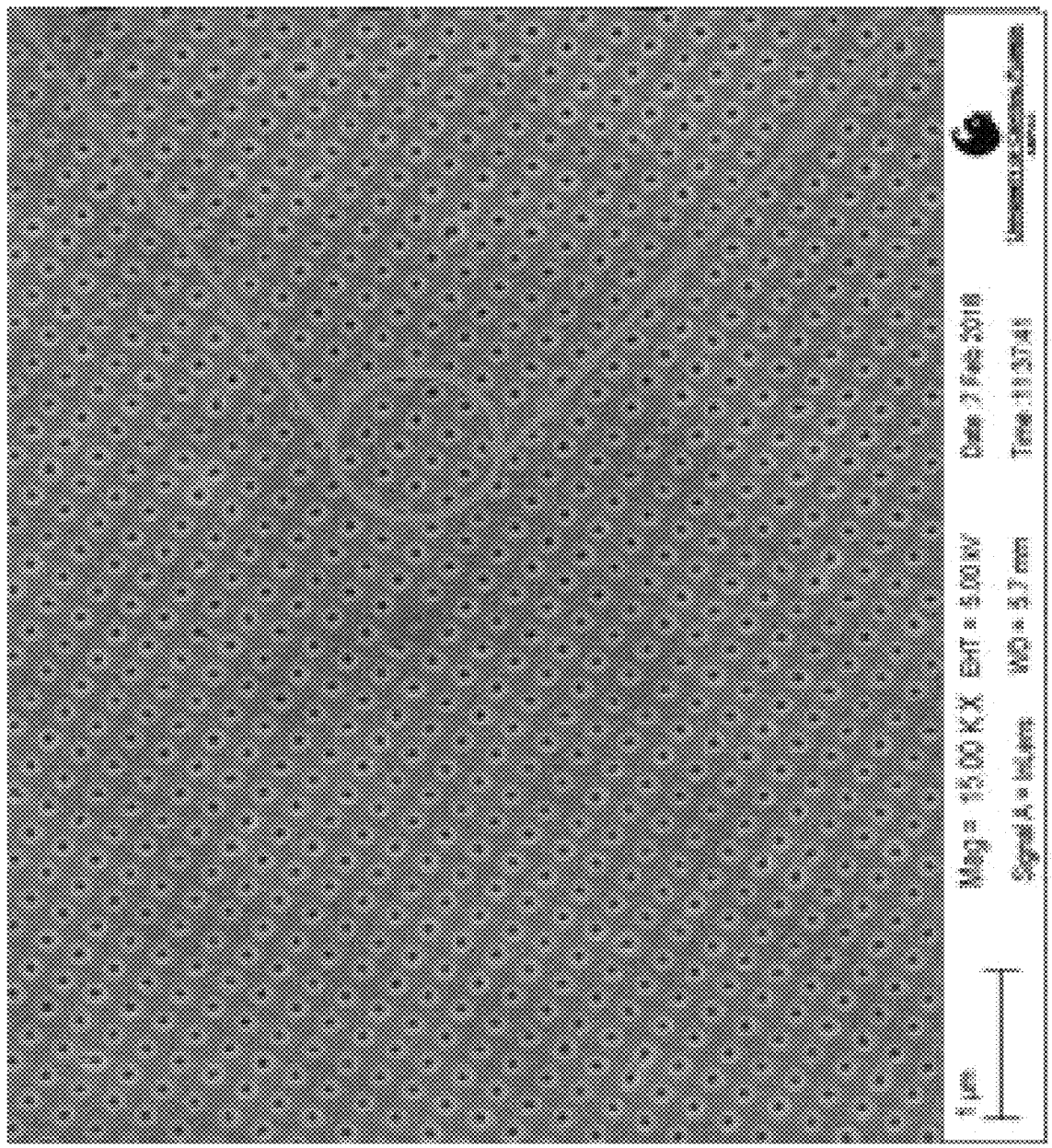
FIG. 7: is an example according to various embodiments, illustrating an SEM image of the nanostructured PAN layer of FIG. 6.
Figure 8:
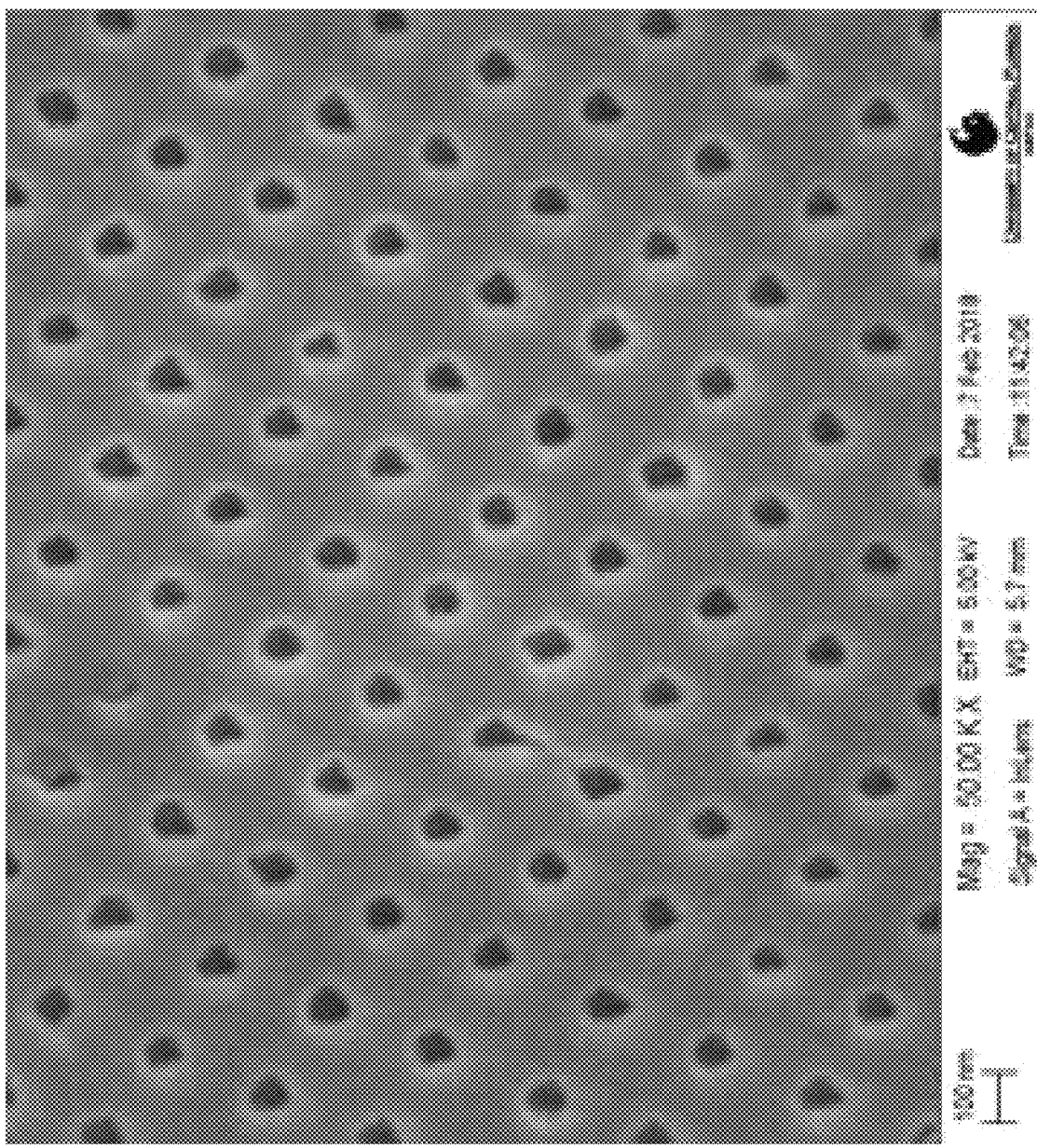
FIG. 8: is an example according to various embodiments, illustrating an SEM image of the nanostructured PAN layer of FIGS. 6 and 7.

FIG. 6 is an example according to various embodiments, illustrating a scanning electron microscope (SEM) image of a finger of the interdigitated electrode deposited on the nanostructured polymer layer of PolyAcryloNitrile (PAN). FIG. 7 is an example according to various embodiments, illustrating an SEM image of the nanostructured PAN layer of FIG. 6. FIG. 8 is an example according to various embodiments, illustrating an SEM image of the nanostructured PAN layer of FIGS. 6 and 7.

Figure 9:
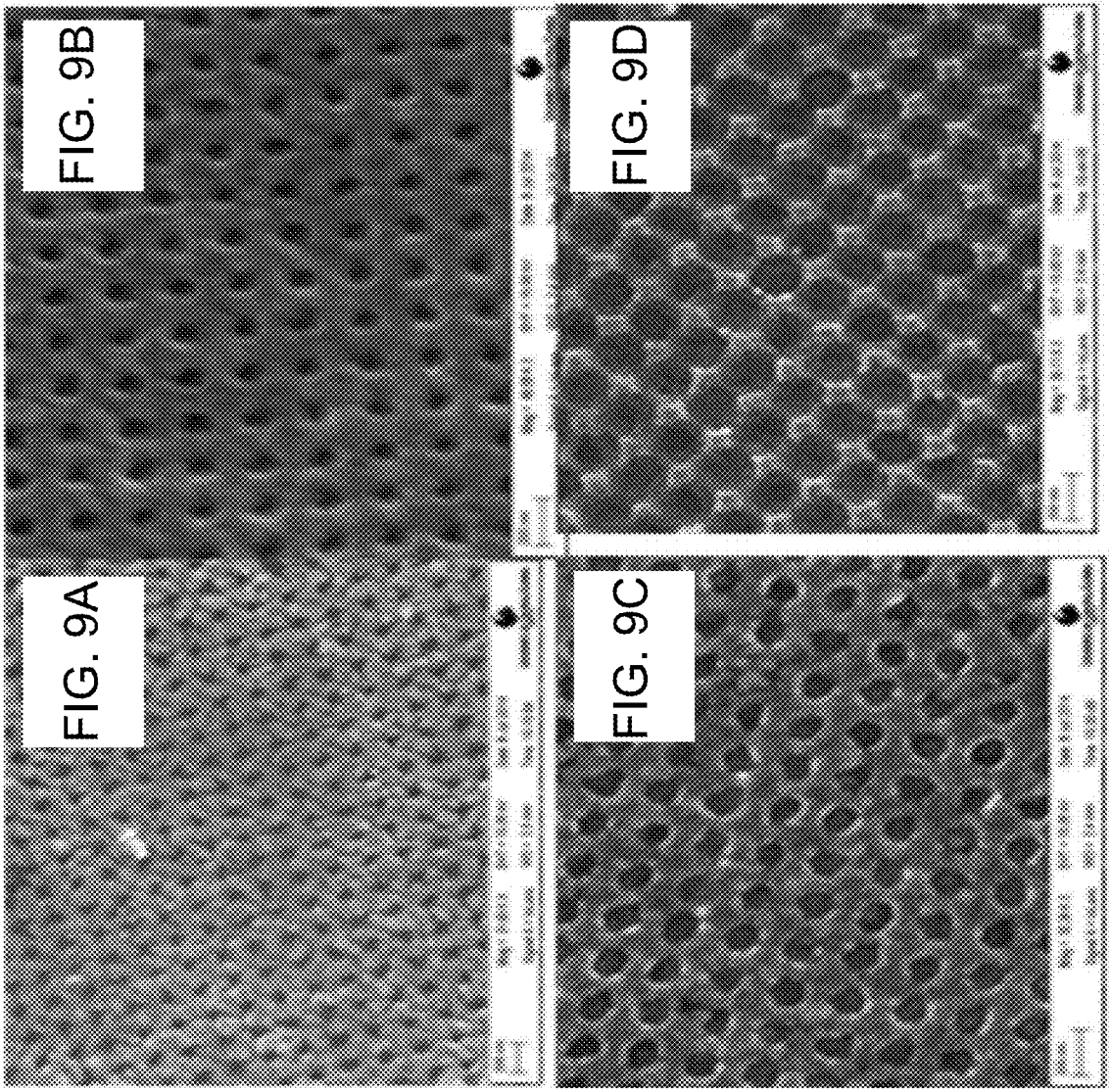
FIG. 9A: is an example according to various embodiments, illustrating an SEM image of printed plasmonic nanohole arrays having an average diameter or size of about 57+/−9 nm.
FIG. 9B: is an example according to various embodiments, illustrating an SEM image of printed plasmonic nanohole arrays having an average diameter or size of about 74+/−9 nm.
FIG. 9C: is an example according to various embodiments, illustrating an SEM image of printed plasmonic nanohole arrays having an average diameter or size of about 105 nm.
FIG. 9D: is an example according to various embodiments, illustrating an SEM image of printed plasmonic nanohole arrays having an average diameter or size of about 136+/−16 nm.
Figure 10:
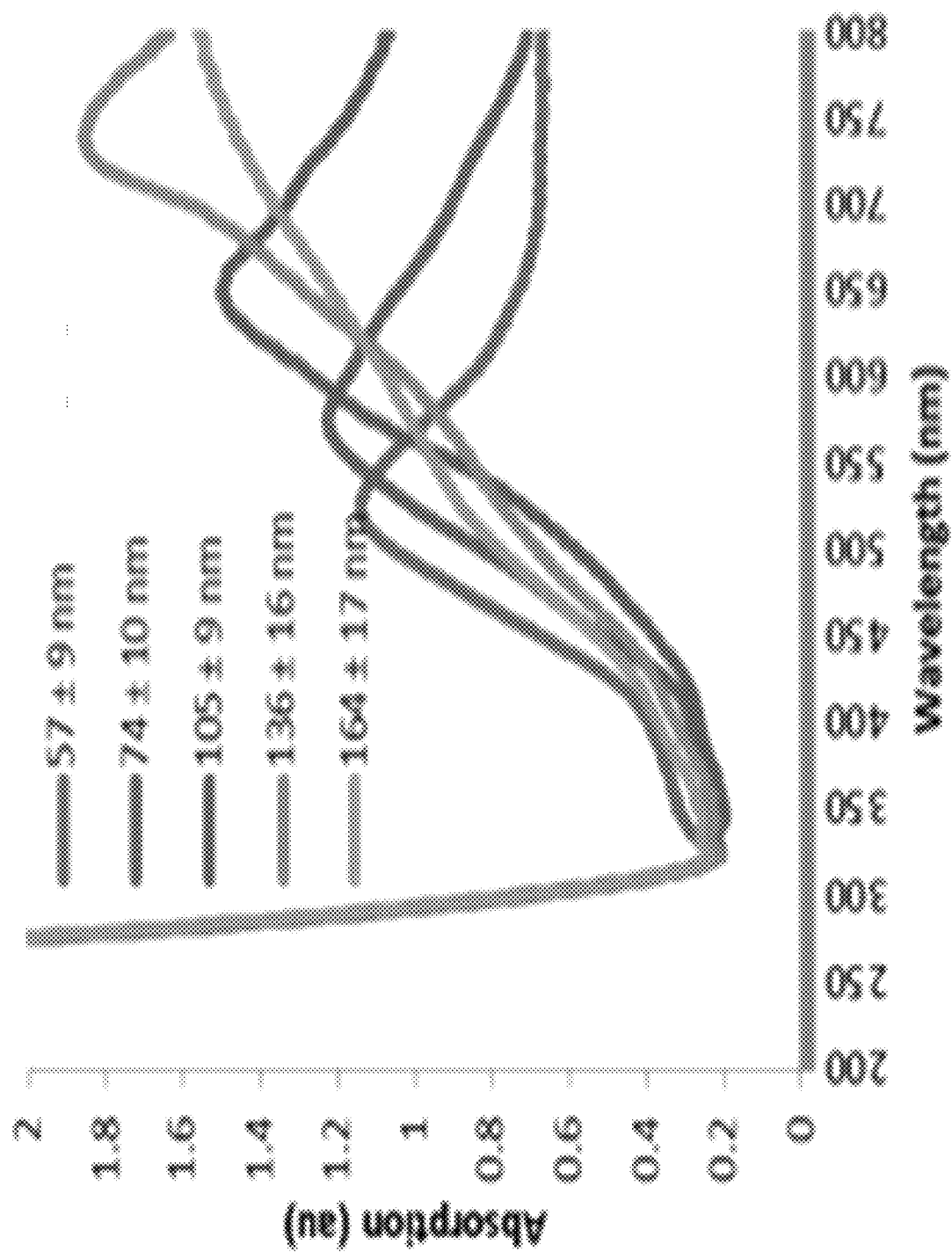
FIG. 10: is an example according to various embodiments, illustrating plasmonic resonance curves of the nanohole structures having various average diameters or sizes.

Various embodiments employ a spin-coating technique to fabricate nanohole array from a one-time e-beam fabricated Si mold on a polyacrylonitrile (PAN) polymer as given in the FIGS. 9A, 9B, 9C, 9D and FIG. 10. More specifically, a set of silver plasmonic substrates tuned to achieve different plasmon resonance frequency and their respective extinction peaks are given in FIGS. 9A, 9B, 9C, 9D and FIG. 10. FIG. 9A is an example according to various embodiments, illustrating an SEM image of printed plasmonic nanohole arrays having an average diameter or size of about 57+/−9 nm. FIG. 9B is an example according to various embodiments, illustrating an SEM image of printed plasmonic nanohole arrays having an average diameter or size of about 74+/−9 nm. FIG. 9C is an example according to various embodiments, illustrating an SEM image of printed plasmonic nanohole arrays having an average diameter or size of about 105 nm. FIG. 9D is an example according to various embodiments, illustrating an SEM image of printed plasmonic nanohole arrays having an average diameter or size of about 136+/−16 nm. FIG. 10 is an example according to various embodiments, illustrating plasmonic resonance curves of the nanohole structures having various average diameters or sizes.

Figure 11:
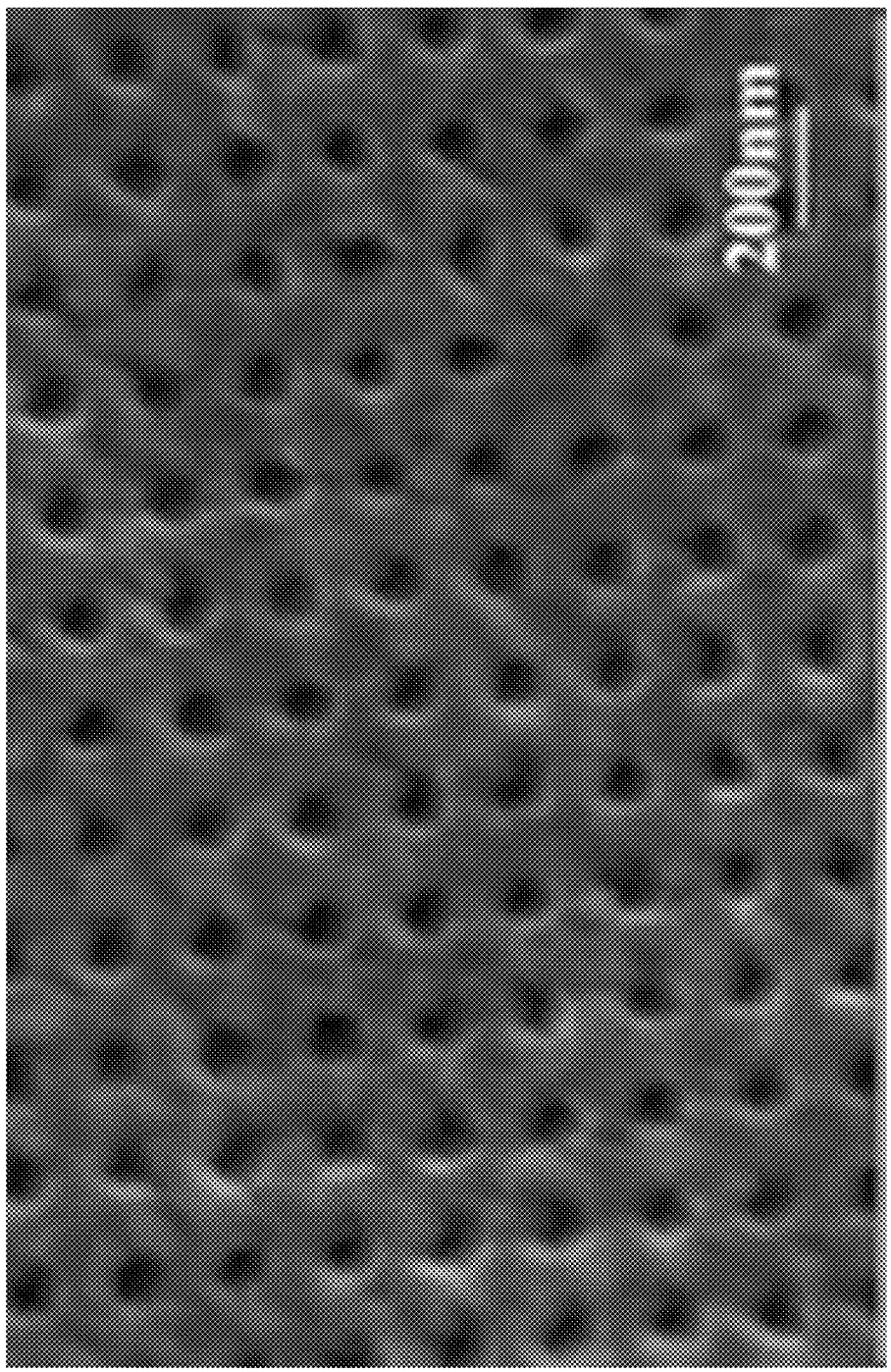
FIG. 11: is an example according to various embodiments, showing an SEM image of printed plasmonic nanohole arrays.

To produce the structures shown in FIGS. 9A, 9B, 9C, 9D, PAN solution was spin-coated on the Si mold by a spin-on nanoimprinting technique. The film was cured at about 130° C. and transferred to a glass substrate by peeling off the film. An oxygen plasma cleaner with different etching times was then used to tune to the required hole size. A silver/gold metal may then be deposited onto this structure to achieve the plasmonic effect. Various embodiments utilize the change in impedance due to plasmonic effect with millimeter-scale IDEs and cell-like materials. Impedance electrodes were defined on top of the printed plasmonic nanostructures shown in FIGS. 9A, 9B, 9C, 9D. Shadow masks were fabricated utilizing a CNC micromill on stainless steel substrates and were aligned with the printed plasmonic substrates for metal definition in an e-beam evaporator for the IDE fabrication. The definition of the plasmonic nanostructures was apparent by the change in color of the IDEs with varying thicknesses of the deposited gold on the devices as shown in FIGS. 11, 12, 13, 14, and 15. FIG. 11 is an example according to various embodiments, showing an SEM image of printed plasmonic nanohole arrays.

Figure 13:
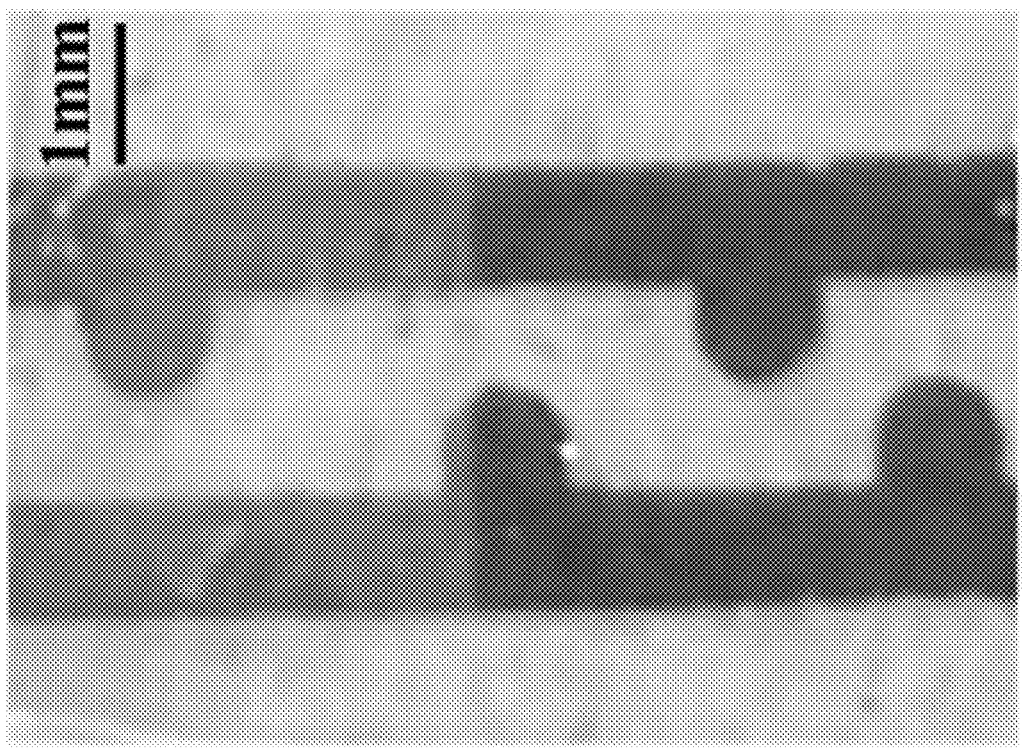
FIG. 13: is an example according to various embodiments, showing a photograph of electrodes having a plurality of interdigitated fingers.
Figure 14:
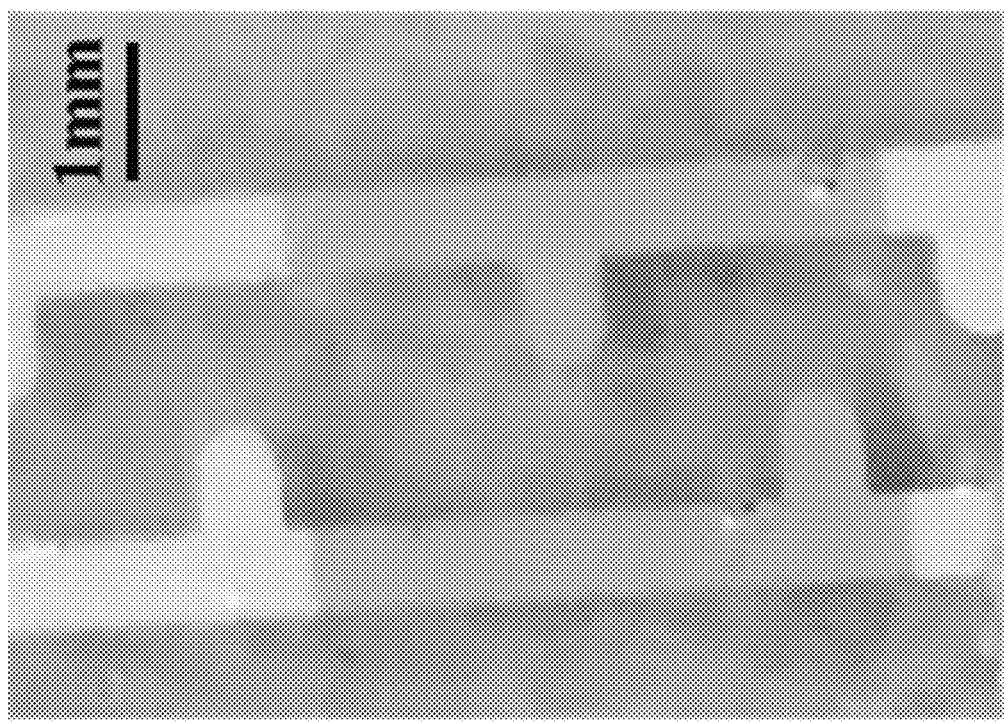
FIG. 14: is an example according to various embodiments, showing a photograph of electrodes having a plurality of interdigitated fingers
Figure 15:
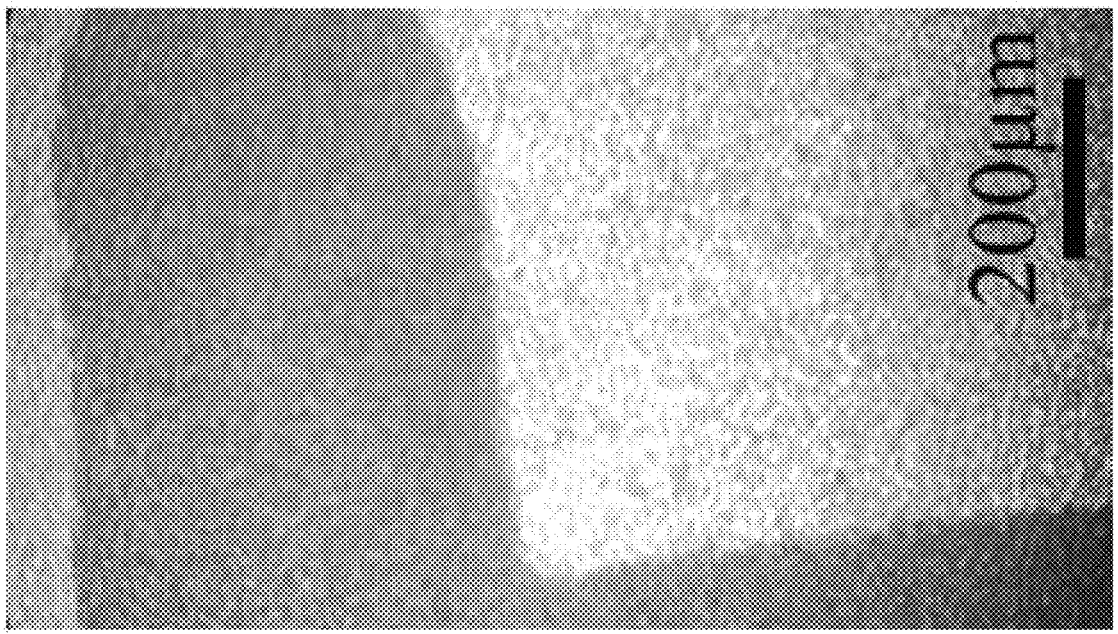
FIG. 15: is an example according to various embodiments, illustrating an optical image of cardiomyocytes on a pIDE.
Figure 16:
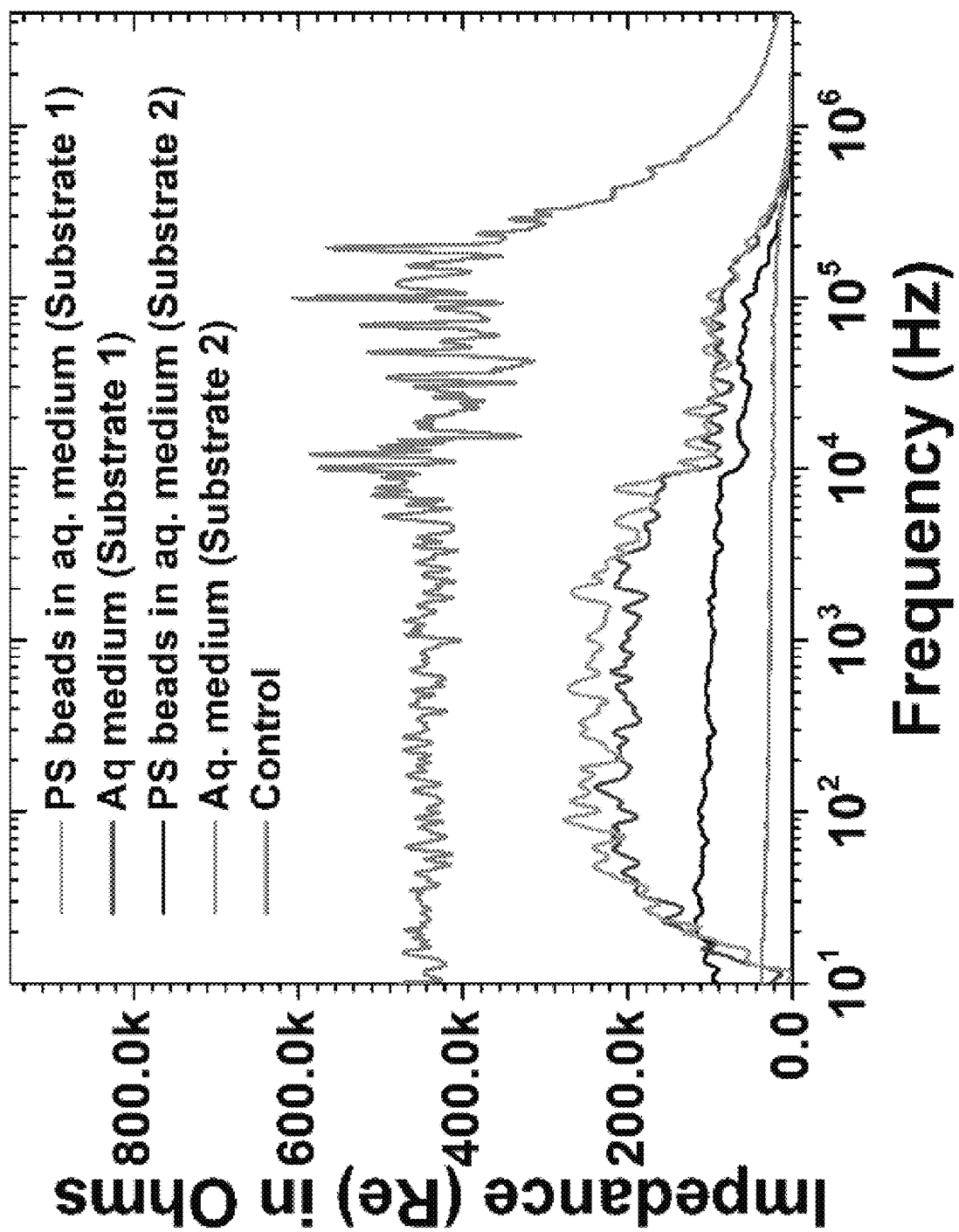
FIG. 16: is an example according to various embodiments, illustrating an impedance spectrum of plasmonic interdigitated electrodes and a control with no plasmonics.
Figure 17:
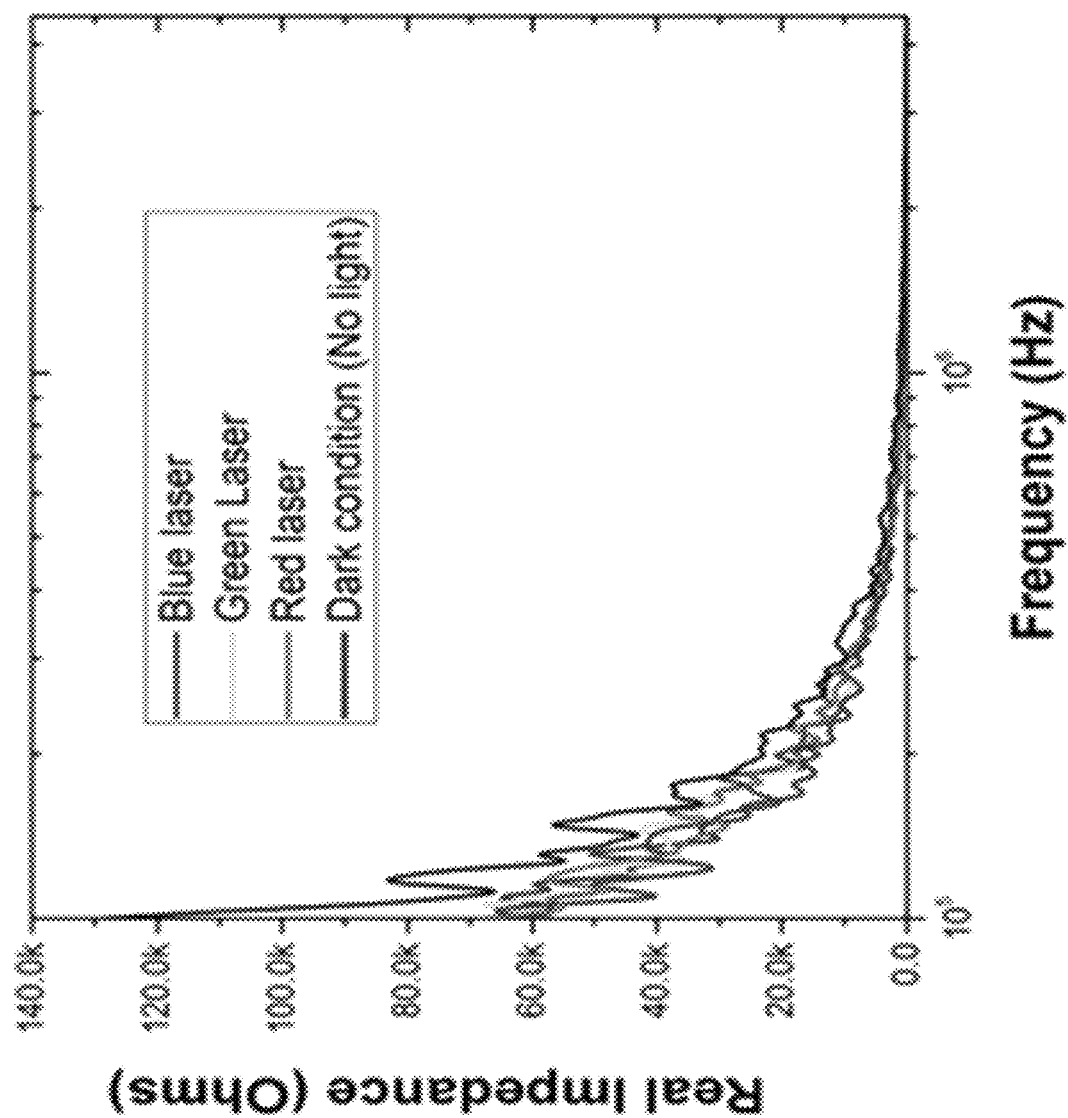
FIG. 17: is an example according to various embodiments, illustrating impedance spectrum measurements of plasmonic interdigitated electrodes under dark and light conditions depicting subtle variations for the different laser sources used.

FIG. 13 is an example according to various embodiments, showing a photograph of electrodes having a plurality of interdigitated fingers. FIG. 14 is an example according to various embodiments, showing a photograph of electrodes having a plurality of interdigitated fingers. FIG. 15 is an example according to various embodiments, illustrating an optical image of cardiomyocytes on a pIDE. These optical micrographs, of millimeter scale, show full packaged plasmonic interdigitated electrodes. FIGS. 13 and 14 show the plasmonic characteristic colors for the two different thickness of gold deposited. FIG. 13 shows 30 nm—green. FIG. 14 shows 50 nm—red. These units were subsequently wire bonded with conductive epoxy and a 3-D printed culture well was affixed for the characterization of any analyte deposited on the impedance electrodes with the underlying plasmonic nanostructures. Polystyrene beads (~1 um in size) were deposited in solution in lieu of cells for the demonstration of an impedance shift using the BODE impedance analyzer. As can be seen in FIGS. 16 and 17, the devices with the varying thicknesses of gold have a different impedance signature in the 10-100 kHz range when compared to a control IDE with no plasmonic nanostructures. FIG. 16 is an example according to various embodiments, illustrating an impedance spectrum of plasmonic interdigitated electrodes and a control with no plasmonics. FIG. 17 is an example according to various embodiments, illustrating impedance spectrum measurements of plasmonic interdigitated electrodes under dark and light conditions depicting subtle variations for the different laser sources used. FIGS. 16 and 17 show data procured from the millimeter-scale plasmonic Interdigitated Electrodes shown in FIG. 12. These are full spectrum impedance measurements of a control PAN IDE with no plasmonic nanostructures and PIDEs with different thickness of gold. The devices were subject to a sample analyte (polystyrene beads) modeling cells. The impedance response to various structures is clearly visible. On the right, the full spectrum impedance measurement is depicted under dark and light conditions depicting subtle variations for the different laser sources used. Light was additionally shown during the impedance measurement to see the added plasmonic effect. FIGS. 16 and 17 further depicts a change in the impedance values in the 100 kHz to 1 MHz range with light. This data demonstrates the change in response may correspond to activation of the plasmonic nanostructures tuned to their resonance peak.

Example 1

PAN plasmonic nanomachined layers (1 cm×1 cm; substrate 1: nanohole Ø: 100 nm, pitch: 200 nm; substrate 2: nanohole Ø: 50 nm, pitch: 200 nm; FIG. 1) were fabricated, tuned, and transferred onto a glass substrate. Gold IDEs (800 μm wide; 1 mm long; 1 mm pitch with thickness of 50 nm and 30 nm) were deposited on the plasmonic substrates through shadow masks fabricated with a micromilling process of metal sheets. A 3D printed hollow culture well (10 mm inner diameter; 10 mm tall) was printed and affixed with EpoTek 353ND epoxy to complete the PIDE device fabrication and assembly. Dulbecco's PBS (1×) was used as the electrolyte and polystyrene (PS) latex beads of 1.1 μm particle size and concentration of 0.1 mg/ml in DI water were used as a cell-like material for the impedance and optical analysis of the PIDEs.

Figure 18:
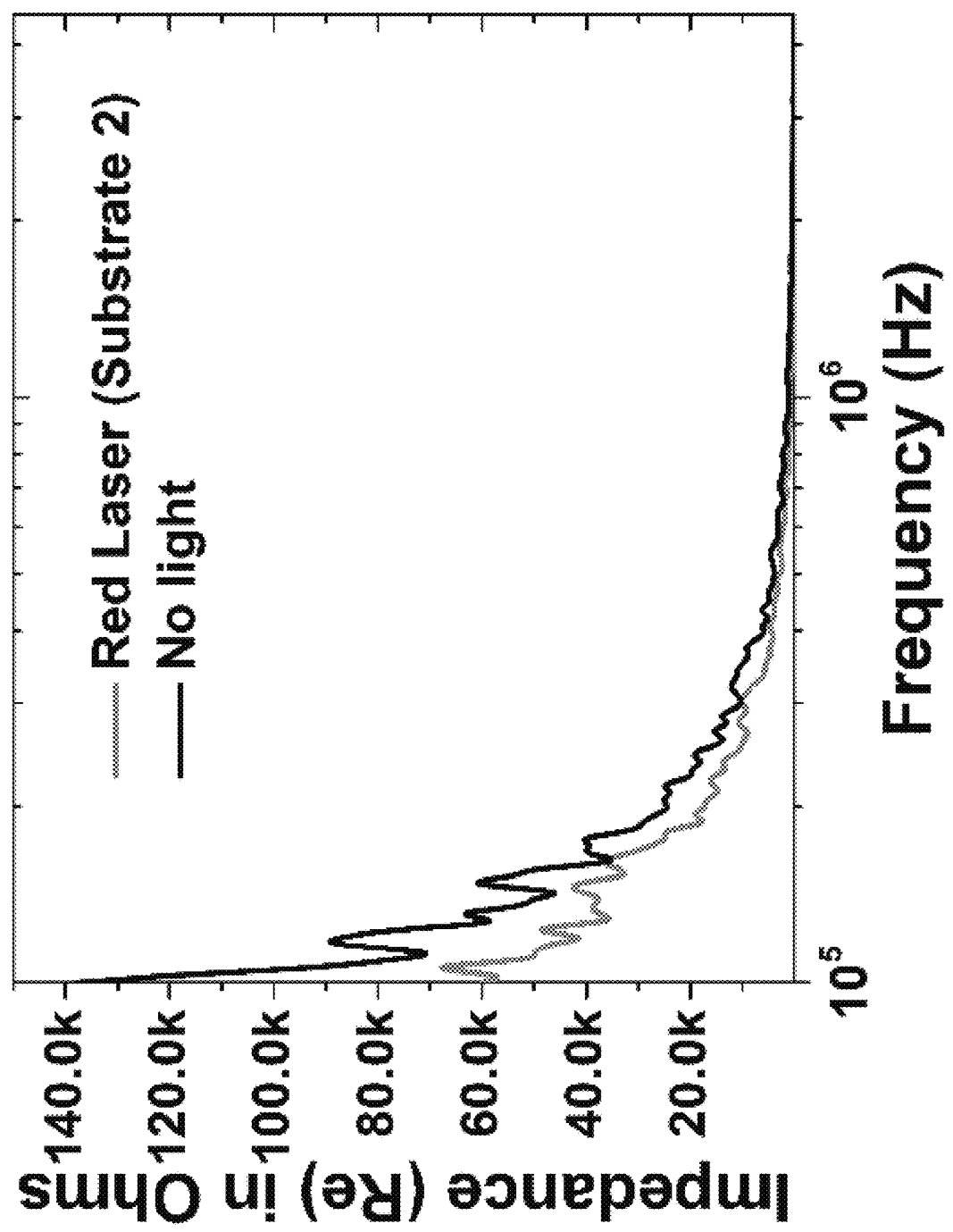
FIG. 18: is an example according to various embodiments, illustrating impedance spectrum measurements of plasmonic interdigitated electrodes under illumination.

FIG. 11 is an example according to various embodiments, showing an SEM image of printed plasmonic nanohole arrays. FIG. 12 is an example according to various embodiments, showing a photograph of a plasmonic interdigitated electrode assembly. FIG. 13 is an example according to various embodiments, showing a photograph of electrodes having a plurality of interdigitated fingers. FIG. 14 is an example according to various embodiments, showing a photograph of electrodes having a plurality of interdigitated fingers. FIG. 15 is an example according to various embodiments, illustrating an optical image of cardiomyocytes on a pIDE. The nanoscale plasmonic nature of the PAN substrate is evident from FIGS. 11, 12, 13, 14, and 15. FIGS. 13, and 14 show a distinct green and orange color in the portions where the IDE has been defined. FIG. 16 is an example according to various embodiments, illustrating an impedance spectrum of plasmonic interdigitated electrodes and a control with no plasmonics. FIG. 16 depicts the real part of the complex impedance for two different PIDE devices with and without PS beads in deionized water with comparisons to a control PAN IDE device with no plasmonics depicting a clear distinction. Within the PIDE devices, the impedance is seen to be greater with PS beads due to the increased electrolytic resistance from the interaction of the PS beads and the nanoscale openings. However, the two distinct signatures of PIDEs (having same IDE geometry) indicates variability in nanoscale geometry with different thicknesses of deposited gold in the PIDE fabrication resulting in a clear difference in the full spectrum impedance of both the devices. FIG. 18 is an example according to various embodiments, illustrating impedance spectrum measurements of plasmonic interdigitated electrodes under illumination. FIG. 18 shows the reduction in impedance when the device is illuminated with a red laser (630-660 nm) which may be attributed to the enhanced capacitance in the plasmonic portions of the PAN substrate under illumination. At these wavelengths, the PIDE sensor can clearly be utilized for cellular biosensing with improved sensitivity and no interference from biosignals and noise which are typically attributed to a much lower wavelength.

Example 2

This example relates to the development of cost effective, printed plasmonic substrates for real-time impedance and plexitonic studies. A reliable and cost-effective nanofabrication method to develop plasmonic structures for producing plasmonic substrates with exceptional quality is described.
Fabricating Printed Plasmonic Structures This example aims to perform FDTD simulation to optimize the plasmonic structures with more than $10^5$ EF to achieve maximum signal from impedance measurements. The focus is to simulate a nanostructure which can provide maximum LSPR field as well as Mie scattering. Based on these simulations this example aims to fabricate a one-time required silicon mold by an e-beam technique. The polymer-based plasmonic nanostructures will be developed in four simple steps: spin coating, peeling off, and silver/gold deposition as schematically shown in FIGS. 3A, 3B, 3C, and 3D, which shows a fabrication process flow depicting the various steps in the definition of nano-holes of PAN on a glass substrate. This approach permits high throughput, large area fabrication of plasmonic substrates with great versatility. Unlike, other nanoimprinting techniques, this technique does not require high pressure, temperature or UV light for printing and nanostructures can be fabricated in a few minutes.

Figure 19:
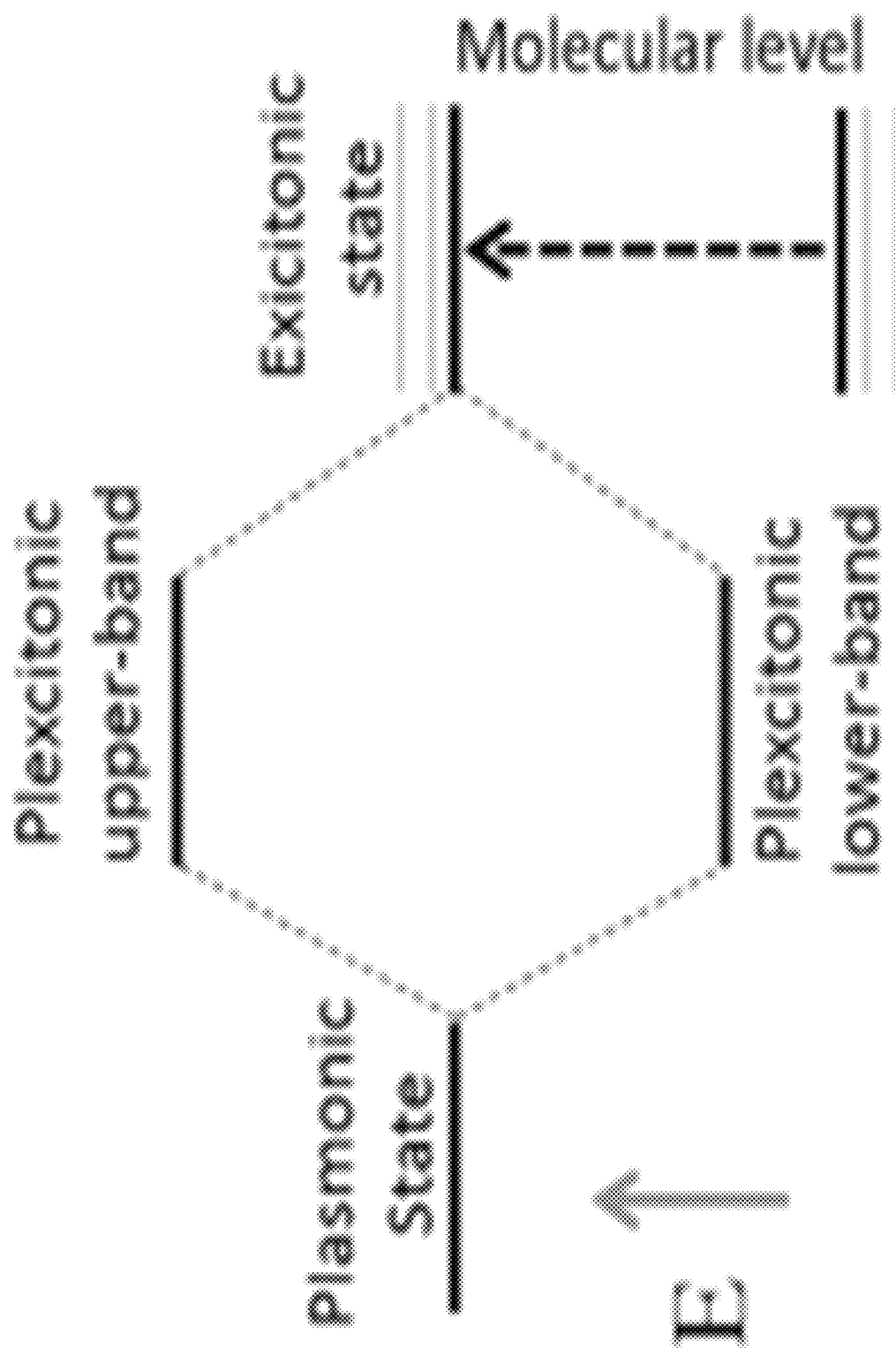
FIG. 19: is an example according to various embodiments, illustrating a schematic depicting splitting of absorption peaks forming low and high energy states.

In plasmonics, the term "hot spot" has been often used to describe the location on the plasmonic substrate where there is a concentration of plasmonic field. As a result of this field enhancement, the physical properties of molecules near these hotspots are enhanced many times. Plasmonic field concentration on a given nanostructure can be simulated using FDTD simulation software like Lumerical FDTD Solution. A fourth order Gaussian curve is used to profile the plasmonics on the nanohole array structure. FIGS. 25A, 25B, 25C, and 25D illustrate FDTD calculated enhancement factor (EF) profiles of the structures at different cross-sections of the nanohole array substrate. More specifically, FIG. 25A is an example according to various embodiments, illustrating calculated enhancement factor (EF) profiles of a nanohole array substrate at different cross-sections used for simulation of the plasmonic field concentration on the nanohole array substrate using Finite-Difference Time-Domain (FDTD) simulation software. FIG. 25B is an example according to various embodiments, illustrating schematic diagrams of the index profile of the simulated structure referenced with respect to FIG. 24A. FIG. 25C is an example according to various embodiments, illustrating an EF profile at the middle of a groove where two adjacent holes merge of a 164 nm nanohole array substrate as referenced with respect to FIG. 24A. FIG. 25D is an example according to various embodiments, illustrating an EF profile cut along x at z=32 nm of the 2D profile in FIG. 24C. For example, in the case of 164 nm hole array sample, the local maximum EF was determined to be 38.87 located in a groove where two adjacent holes' merge. The cross-sectional plot of this hot spot is shown in FIG. 25D. The local maximum EFs of other samples were also simulated in a similar fashion. These computationally derived maximum local EFs are plotted against their bare plasmon resonance for comparison (FIG. 25B).
Tuning the Plasmonic Resonance Absorption Frequency This example implements an easy-to-adopt fabrication scheme to make tunable plasmonic structures which involves tuning plasmonic nanostructures by optionally optimizing the nanohole size using a simple and inexpensive plasma etching process (FIG. 3D) using a commonly available plasma cleaner. Excellent wavelength tuning was achieved in less than 5 minutes. The detection technique, according to various embodiments, is based on the principle that the electromagnetic field due to LSPR of the substrates influences the AC potential applied during the impedance measurement. It is the AC component of the LSPR that influences the impedance of the analyte on the PIDEs. Therefore, the tuned plasmon resonance structures will maximize the effect of plasmon resonance on the impedance. In addition, it is required to tune the plasmonic resonance wavelength to the electronic absorption wavelength of the labelled dye for plexitonic detection.
Designing Plasmonic Based IDEs for Simultaneous Impedance and Optical Measurement Plexitonic substrates may be used for molecular detection in single cells. The hypothesis is that if plexitonic substrates are used for dye labelled biomolecular detection, Raman and fluorescence signals can be highly enhanced. FIG. 19 is an example according to various embodiments, illustrating a schematic depicting splitting of absorption peaks forming low and high energy states. A splitting of the absorption peak of the dye can also be observed due to the formation of a high energy and low energy plexitonic states as shown in the FIG. 19, which is a schematic depicting splitting of absorption peaks forming low and high energy states. This is based on the principle that the coupling between the plasmons of the plasmonic structure and excitonic mode of the dye results in a hybridized energy state that highly enhances these signals. According to various embodiments, this can lead to detection of concentrations of individual molecules in a single cell using the plasmonic detection technique.

Example 3

This example relates to the development of interdigitated microelectrodes and a demonstration of non-invasive single cell analysis.

Various embodiments relate to impedance based systems that may be utilized in the monitoring of cells that are cultured on top of the electrodes. Such embodiments are useful in biosensing, toxicity and pharmacological applications. This example shows the development of technologies to accomplish the following specific goals: (1) development of suitable metallization technologies for the definition of various interdigitated geometries for PIDEs; (2) package the PIDE sensors for cellular analysis; (3) evaluate the biocompatibility of the electrode arrays and the nanostructured materials with suitable cardiomyocyte cultures; (4) evaluate the electrical and plasmonic response of cardiotoxicity inducing compounds to develop a non-invasive analysis technology for single cells and networks of cells.

Development of Metallization Technologies for Interdigitated Electrodes (IDEs)

Interdigitated Electrodes (IDEs) typically have two electrodes with external access through bond pads and metal traces with "fingers" that enable various features. Metal electrodes are deposited in these various shapes and sizes that can be modified depending on the application. Technologies such as lift-off, deposit and etch or shadow mask can be used in the definition of such electrodes. Various embodiments, utilize shadow mask metallization in order to minimize processing steps on top of plasmonic nanostructures as depicted schematically in FIGS. 4A, 4B, and 4C, which show a schematic of the fabrication process flow for structuring electrodes on plasmonic nanostructures to create PIDEs. FIG. 4A shows the immobilization of a plasmonic nanostructure on a substrate (e.g. glass). FIG. 4B shows fabrication and alignment of a shadow mask with the IDE pattern. FIG. 4C shows metal deposition using sputter or e-beam coating to finish the fabrication of PIDE. Shadow mask technology or microstenciling can play a key role in the fabrication of biological devices such as cellular scaffolds, biosensors, microfluidic devices, pace makers and therapeutic systems because this technology can be used to pattern both biological and non-biological materials repeatedly, rapidly, consistently and cost effectively. Microstencils or shadow masks are typically thin layers of material (e.g. silicon, glass, polymers, resins etc.) that are micro/nanomachined to have patterned apertures for the controlled deposition of materials. Various embodiments provide a microstenciling technology with the laser micromachining of polymers utilizing the EzLaze 3 multi-modal laser. The use of such a benchtop multi-modal laser offers the design flexibility (features sizes down to 1 um), versatility with various materials that can be fabricated, material matching for thermal and mechanical properties between the shadow mask and the plasmonic nanostructure and lastly cost-effective rapid translation from design to a manufactured stencil mask. The printed plasmonic nanostructure from Example 2 aligned with the shadow mask (various electrode sizes from 1 um to 500 um may be designed and fabricated) and metals such as gold and silver may be deposited utilizing sputter or e-beam metallization. The alignment of the structures is important and corresponding features for efficient alignment are defined during the fabrication of the printed plasmonic nanostructure and the shadow mask.

Packaging the IDEs for Cellular Analysis

Irrespective of the feature sizes of the IDEs, bond pads for external access of the electrodes can be defined on a scale compatible with conductive epoxy bonding of the plasmonic IDEs. Additionally, various culture wells were designed and 3-D printed with and without capabilities for fluidic flow for attachment to the plasmonic IDEs with biocompatible materials such as Poly DiMethyl Siloxane (PDMS). A combination of the culture well and the epoxy bonds ensures that the device is packaged for biocompatibility, full spectrum impedance, plasmonic and plexitonic studies.

Cytocompatibility of the Plasmonic IDEs

The cytocompatibility of plasmonic IDE materials to "on demand" cardiomyocytes (iCells from Cellular Dynamics Inc.) was ascertained. Such an evaluation with materials involved in the construction of the PIDEs such as PAN, thin film metal and 3-D printing resin with respect to the cardiomyocytes chosen for the cell culture will be performed with techniques such as optical cell counting, and a luminescent ATP assay. This cytocompatibility test was performed with cardiomyocytes cultured on the materials set for at least 7 days in vitro (DIV). Optimization of the surface coating on the PIDEs for cell culture will additionally be performed during this biological analysis.

Impedance Analysis of the Plasmonic IDEs for Measurement of Network Cytotoxicity The PIDE, according to various embodiments, enables a cardiotoxicity assay utilizing "on demand" human cardiomyocytes (iCells from CDI). These cells may be plated on the PIDEs that have been coated with fibronectin and incubated first prior to the seeding of the cardiomyocytes. Media may be added subsequently and the devices are incubated with recommended media changes. As suggested by the manufacturer, the impedance recordings may be performed 10-14 days after cell plating utilizing a BODE impedance analyzer. Full spectrum impedance data may be collected and subsequently a calcium channel blocker (Nifedipine) may be added and the impedance change from the baseline is immediately measured. The data from the impedance measurements may be repeated (N=6 for a single experiment) and analyzed utilizing external software (MATLAB or Origin) routines. Additional data may be collected for various concentrations of cells and the impedance data may be analyzed to ascertain whether single cell specificity is achievable with an impedance metric. Additional compounds such as FPL64176, a calcium channel activator and verapamil (another calcium channel blocker) were analyzed utilizing a similar technique for furthering the cardiotoxicity analysis.

Plasmonic and Plexitonic Analysis of the PIDEs for Measurement of Single Cell Cytotoxicity Analysis of impedance change with the plasmonic devices may be performed in the presence of the wavelength-based excitation of the plasmonic nanostructures noticed with cell-like structures (polystyrene beads). In this example, a detailed analysis of such a change in the presence of light and the ability to analyze single cells is ascertained. Additional measurements of the UV Vis spectrum, Raman and fluorescent compound tagging of the cells and confocal microscopic analysis of the plasmonic IDEs with cultured cardiomyocytes may be carried out to ascertain single cell and calcium channel isolation specificity due to the plexitonic effect of the nanostructures.

Example 4

The section below describes the design and fabrication of the nIDE device, followed by the details of the assays and impedance measurements.

Design of the nIDEs

Figure 3:
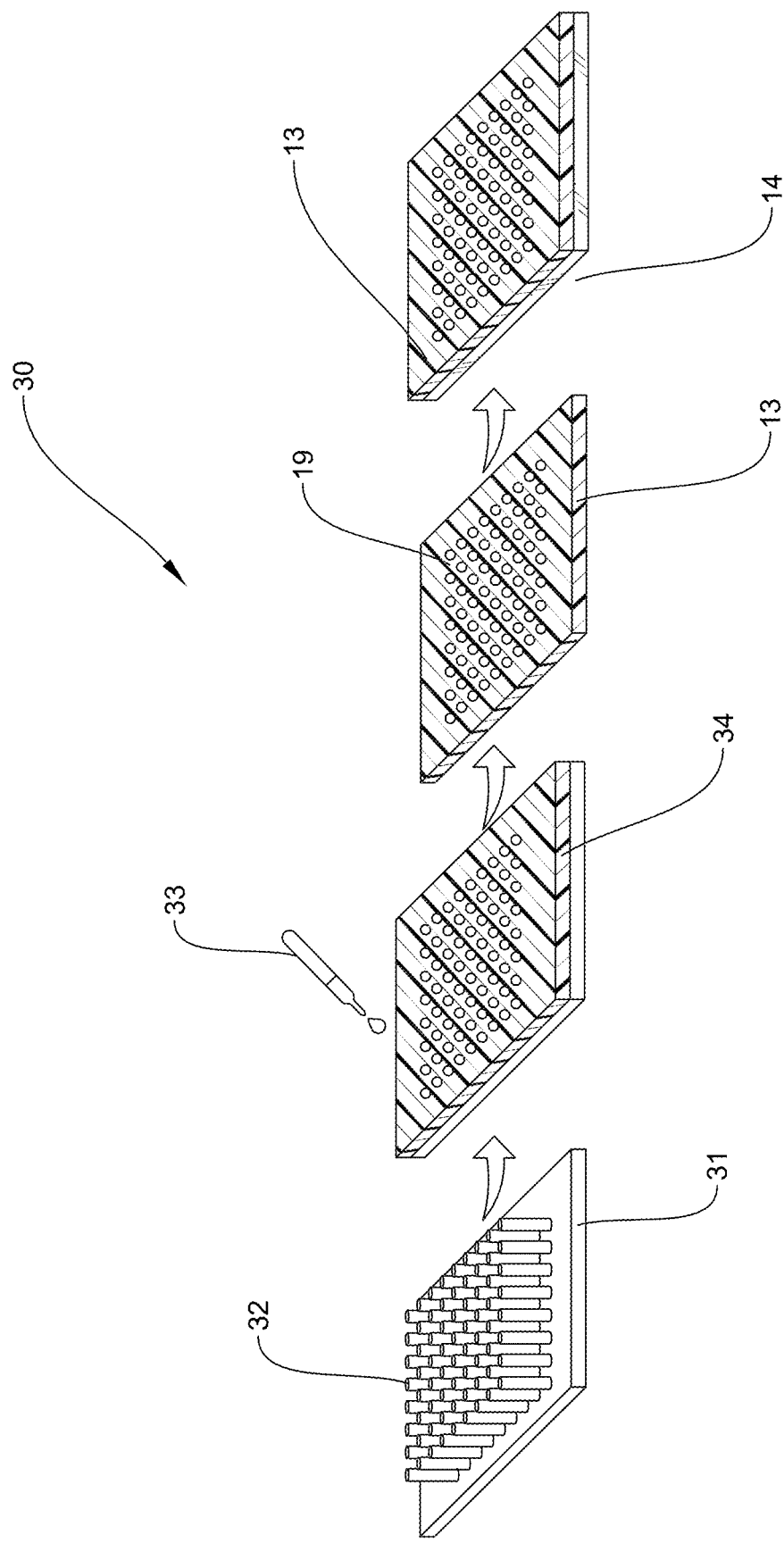
FIG. 3A: is an example according to various embodiments, illustrating a silicon mold having a plurality of nanopillars, which may be used in a method of making a polymeric film having a plurality of nanoholes.
FIG. 3B: is an example according to various embodiments, illustrating a polymer spin-coated onto the silicon mold of FIG. 3A and cured at 150°.
FIG. 3C: is an example according to various embodiments, illustrating a polymeric film having a plurality of nanoholes, which has been peeled off of the silicon mold of FIGS. 3A and 3B.
FIG. 3D: is an example according to various embodiments, illustrating the polymeric film of FIG. 3C after being transferred to a glass substrate.

SolidWorks (Dassault Systems, Waltham, Mass., USA) was used to design the interdigitated electrodes and the culture wells. A schematic of the nIDE device is shown in FIG. 1 and FIG. 3. The gold IDEs are designed to be 800 μm wide and 1 mm long with a pitch of 1 mm and a thickness of 30 nm. The nanostructured chip is comprised of a 5 mm by 5 mm nanomachined PAN layer of 10 μm thickness with 50 nm nanoholes with a pitch of 200 nm. The fully assembled chip is designed to be 10 mm by 10 mm.

Fabrication of the PAN Nanostructures

Various embodiments provide a spin-on nanoimprinting process (SNAP), shown in FIG. 3, to make nanostructures in a very short time. A polymer solution is prepared by dissolving 8 wt % of polyacrylonitrile (PAN, $M_w$=150,000) in dimethylformamide and heated at 150° C. for 5 minutes. The PAN solution was then cooled and spin-coated on a premade Si mold with the inverse of the pattern to be printed. The PAN film was subsequently peeled-off from the mold, transferred to a glass substrate, and cured at 250° C. SNAP technique does not need high temperature, pressure, or any other force during the printing process. Various embodiments provide nanoholes as small as 50 nm on PAN films to make IDEs. Several 100s of nanostructures can be printed from the same master mold without any degradation.

Fabrication of the nIDEs

The 1 mm pitch IDE shadow masks were fabricated using the IDE designs by micromilling. A 90-degree T-8 Mill Tool (150 μm-250 μm diameter; T-Tech, Peachtree Corners, Ga., USA) was spun at 55,000 rpm in a T-Tech J5 Quick Circuit Prototyping Systems to micromill through an 80 μm thick stainless-steel sheet (Trinity Brand Industries, Countryside, II, USA).

The shadow masks were affixed to the 5 mm by 5 mm squares of nanopatterned PAN atop a glass carrier substrate using Kapton tape. A metal film comprised of 30 nm of gold was deposited onto the nanostructured PAN/glass substrate (FIG. 1) using electron beam evaporation (Thermionics Laboratory Inc., Hayward, Calif., USA) to metallize the interdigitated electrodes. The shadow mask was released carefully after the metallization step to reduce the damage to the underlying nanostructures. To package the nIDE device, a 3D printed (Form2, Formlabs, Somerville, Mass., USA) culture well (10 mm inner diameter, 10 mm tall) was dip coated with polydimethylsiloxane (PDMS) in its entirety to improve biocompatibility of the printed resin material, and attached to the substrate using biocompatible 353ND epoxy (EpoTek, Billerica, Mass., USA). Lead wires of sanded copper were subsequently attached to the contact pads using an E2101 electrically conductive silver epoxy (Epotek, Billerica, Mass., USA).

Polystyrene Bead Assay

Polystyrene (PS) latex beads of 1.1 μm particle size and concentration of 0.1 mg/ml in De-Ionized (DI) water (Sigma Aldrich, St. Louis, Mich., USA) were used to emulate a cell like material (FIG. 2). FIG. 2 Fully assembled device being plated with polystyrene beads/cardiomyocytes. The aqueous suspension of PS latex beads was diluted with DI water in a ratio of 1:10 and the diluted solution was uploaded into a syringe and transferred to the culture well of the IDE device. The impedance measurements, from 10 Hz to 10 MHz, were performed on an IDE fabricated on a PAN nanomachined layer with a nanohole diameter of 50 nm and a pitch of 200 nm. The reported impedance values are an average of two devices (N=2).

Cell Culture

Human induced pluripotent stem cell (iPSC) differentiated cardiomyocytes (iCell Cardiomyocytes[2], Cellular Dynamics, Madison, Wis., USA) were used for cell studies. The iPSC cardiomyocytes were kept frozen in liquid nitrogen until they were cultured according to the manufacturer's directions (Cellular Dynamics International, Inc., 2016). To ensure that the cells adhere to the surface, the IDE devices were coated with 5 μL of 1:20 fibronectin (Sigma Aldrich, St. Louis, Mo., USA) and Dulbecco's Phosphate-Buffered Saline (DPBS) without Calcium and Magnesium (Gibco, Waltham, Mass., USA) solution and placed in an incubator (37° C., 7% $CO_2$) for one hour. Cells were thawed and counted to determine the density. This task was performed by mixing 100 μL of cells suspended in media with 0.4% Trypan Blue (Fisher Scientific, Waltham, Mass., USA). A droplet of 100 μL of this solution was subsequently applied to a glass haemocytometer and placed under a 10× microscope objective of a Nikon TE200 Inverted Fluorescence Microscope (Nikon, Tokyo, Japan) for observations. Live, unstained cells were counted in each of four sets of sixteen squares. The cell counts from each of the four sets of squares was averaged and multiplied by 10,000 and then multiplied by 5 to correct for the 1:5 dilution from the Trypan Blue addition. The fibronectin was aspirated and the thawed cells were plated onto the nIDE surfaces (N=8) and 6-well plates (control Polystyrene Plates from Corning, Corning, N.Y., USA) and incubated for one hour (at 37° C. with 7% $CO_2$). A measured droplet of 300 μL of iCell Cardiomyocytes maintenance medium (Cellular Dynamics, Madison, Wis., USA) was subsequently added to each of the eight culture wells. Full media changes occurred every other day.

Eight nIDE devices were densely plated with iCell cardiomyocytes with an average cell density of 310,500 cells per culture well. Each of the two 6-well plates (controls, N=12 wells) were plated with an average cell density of 50,000 cells per well.

Biocompatibility Assay

After one day in vitro (DIV01), nanostructured PAN was placed in the 6-well plate that was plated with approximately 50,000 cardiomyocytes. Biocompatibility studies were performed in these 6-well plates at DIV07 (days in vitro) to ensure that the nanostructured PAN surface was suitably compatible with the iCell cardiomyocyte cell line. This study was performed using the Promega Cell-Titer Glo Luminescent Cell Viability Assay Kit (Promega, Waltham, Mass., USA). A volume of reagent equal to that of the media, 0.5 mL, was added to each culture well and mixed for two minutes to induce lysis. The 6-well plate was incubated at room temperature for ten minutes to stabilize the subsequent measurement of a luminescent signal. Luminescence was recorded using a Tecan Infinite Pro 200 plate reader (Tecan, Männedorf, Switzerland) with the emission wavelength set at 500 nm, the excitation wavelength set at 365 nm, and an integration time of 10 s. The background and control measurements with only media in the culture well and media with cells in the culture well, respectively, were performed in addition to the nanopatterned PAN measurements.

Impedance Measurements

Electric cell-substrate impedance sensing (ECIS) was used to characterize the electrochemical properties of the cell-substrate interface. A low-voltage signal is applied to the nIDEs, which forms ionic currents in the cell culture medium. When cells are located on the nIDEs, these ionic currents are affected by the number, morphology, and adhesion of these cells. Impedance will gradually increase during the normal cell growth and proliferation process; thus, as more cells become attached to the nIDEs, an increase in electrical impedance is expected.

For the impedance measurement, a full spectrum of the frequency range from 10 Hz to 10 MHz, were scanned using BODE 100 impedance measurement station (Omicron Labs, Klaus, Austria) from DIV07 to DIV18. Impedance was normalized using the cell index (CI), Equation 3, where $\Delta Z$ is the change in impedance and $Z_0$ is the background impedance.

$$CI = \Delta Z/Z_0 \quad (3)$$

Since drug-induced cardiotoxicity is of great interest with these biosensors, impedance measurements were additionally performed on the nIDEs with cultured iPSC cardiomyocytes utilizing different concentrations of norepinephrine (Sigma Aldrich, St. Louis, Mo., USA) as a model drug compound. Concentrations of norepinephrine ranging from 0 μM to 250 μM were introduced to the culture well and impedance was measured to detect any changes due to the addition of the model drug. Cell index results from the model drug experiments were further normalized by using the percent cell index (% CI), Equation 4, where $CI_o$ is the cell index with no norepinephrine and $CI_c$ is the cell index for a specific concentration of norepinephrine.

$$\% \, CI = \frac{CI_c}{CI_o} \times 100\% \quad (4)$$

Normalization of cell index calculations is a common feature for such assays with IDEs based approaches and this task was performed to compare the approach of various embodiments with prior art attempts.

Results and Discussions

Figure 20:
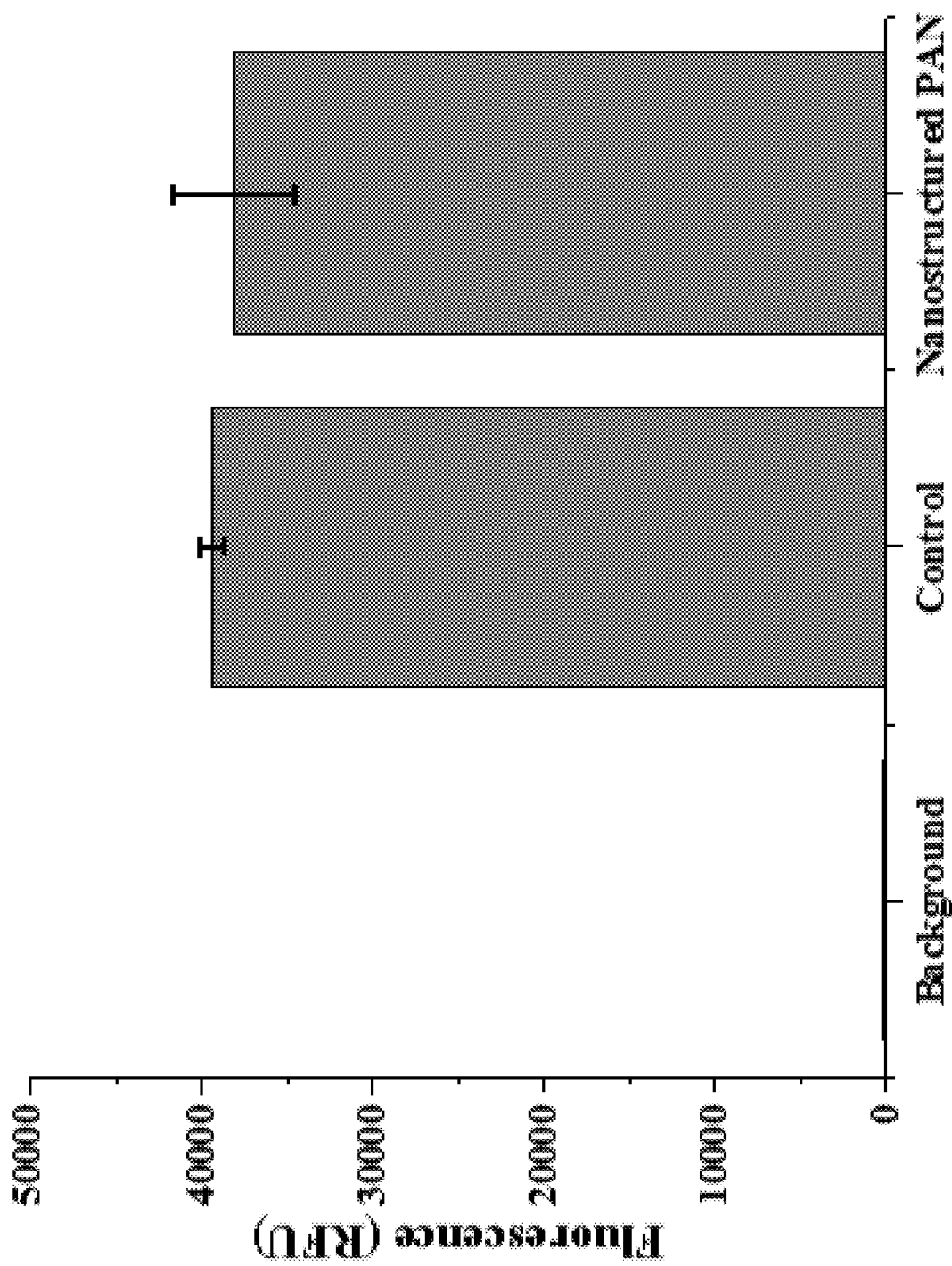
FIG. 20: is an example according to various embodiments, illustrating biocompatibility assay results.

FIG. 20 is an example according to various embodiments, illustrating biocompatibility assay results. FIG. 20 Biocompatibility assay results—The nanostructured PAN substrate shows similar biocompatibility (N=6) to control samples comprised of just cells in a 6-well plate.

Figure 21:
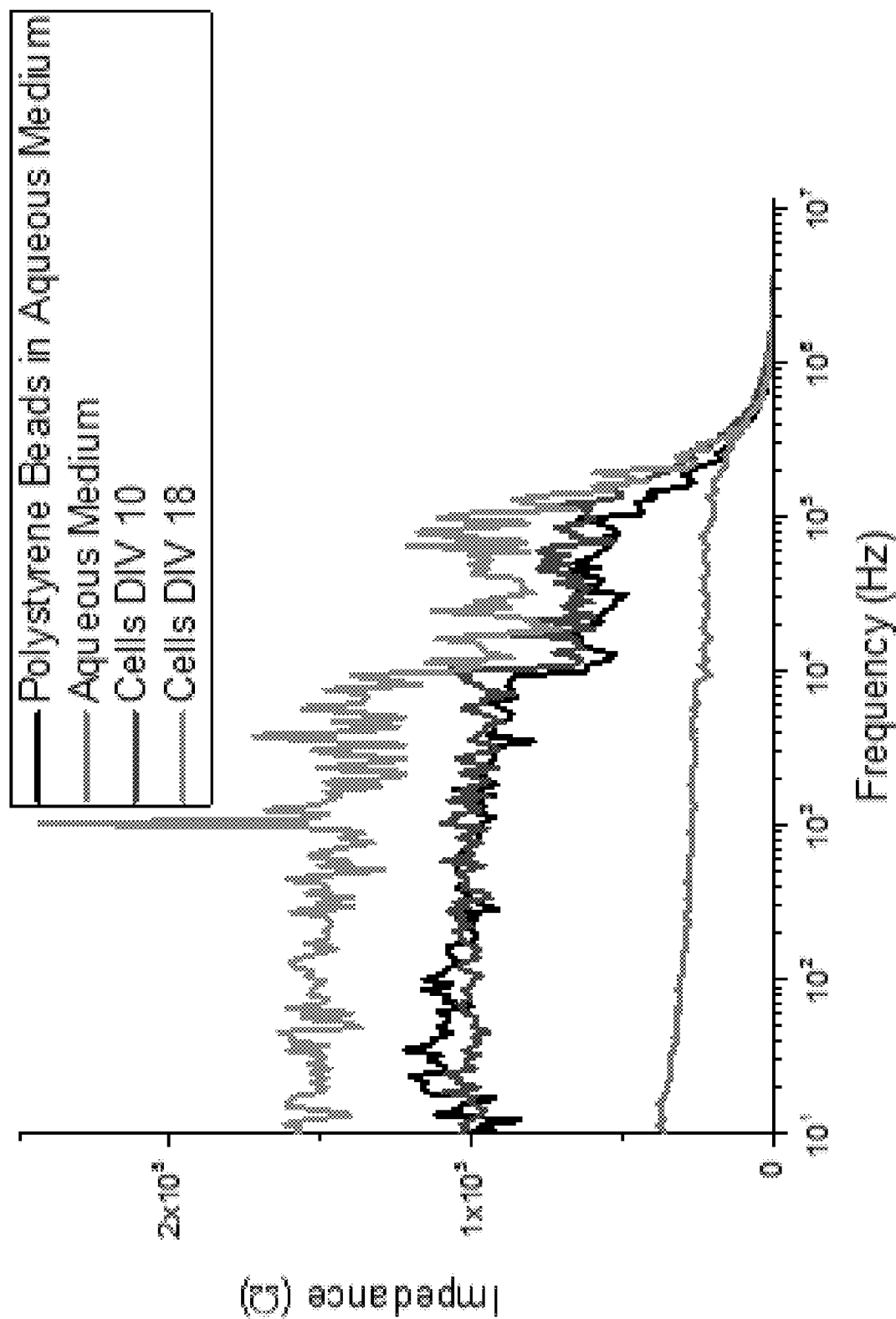
FIG. 21: is an example according to various embodiments, illustrating representative full spectrum impedance measurements of nanostructured interdigitated electrodes (nIDEs) with cardiomyocytes cultured on them.

FIG. 21 is an example according to various embodiments, illustrating representative full spectrum impedance measurements of nanostructured interdigitated electrodes (nIDEs) with cardiomyocytes cultured on them. FIG. 21 Representative full spectrum impedance measurements—The nIDEs with cardiomyocytes cultured on them show an increased impedance from the nIDEs that only have an aqueous medium. In addition, as the cells proliferate an increase in impedance is observed.

Figure 22:
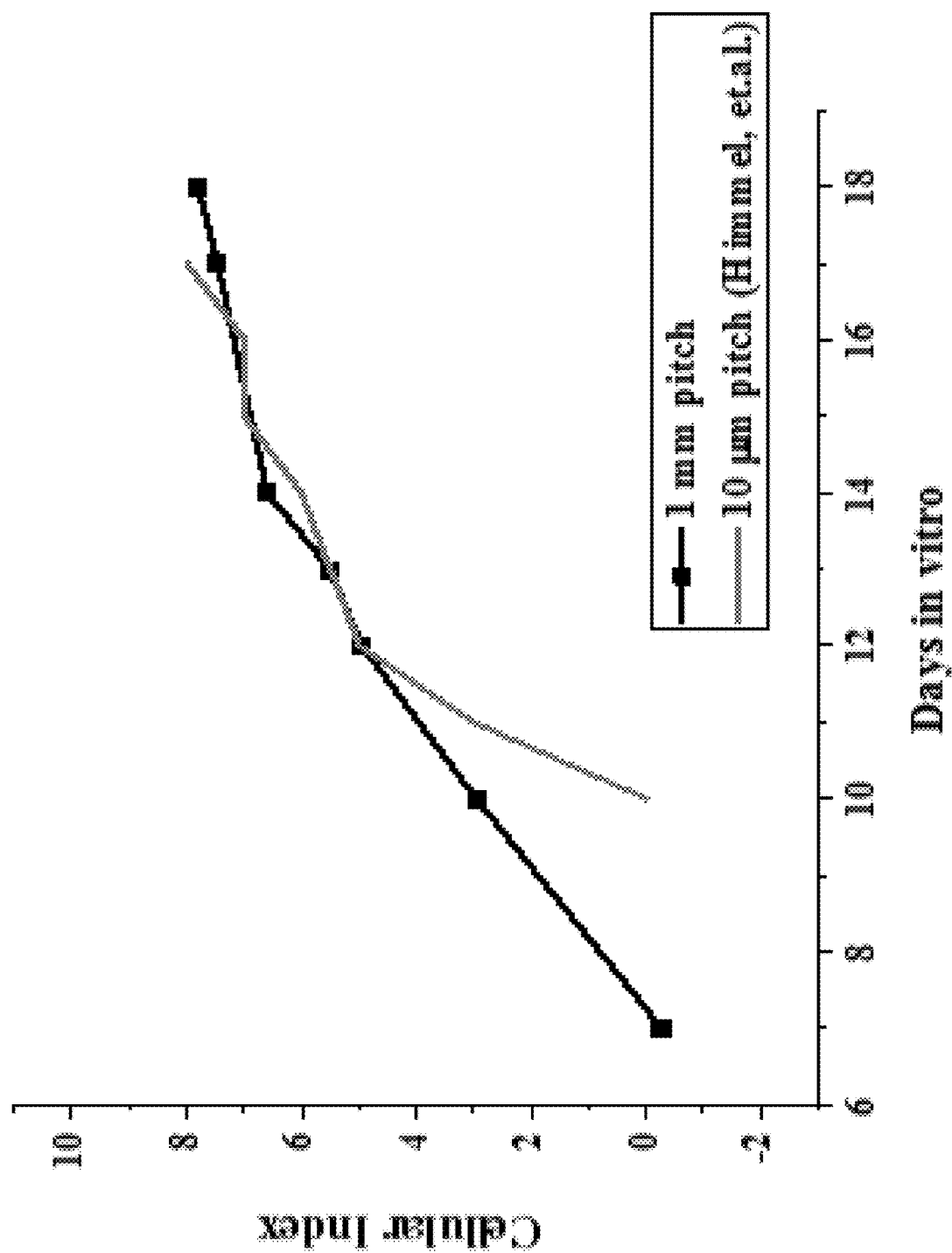
FIG. 22: is an example according to various embodiments, illustrating a chart showing variation of the Cellular Index (CI) of the cardiomyocyte cells, referenced with respect to FIG. 20, cultured on the nIDEs for 18 days.

FIG. 22 is an example according to various embodiments, illustrating a chart showing variation of the Cellular Index (CI) of the cardiomyocyte cells, referenced with respect to FIG. 20, cultured on the nIDEs for 18 days. FIG. 22 Variation of the Cellular Index (CI) of the cells cultured on the nIDEs for 18 days: it was observed that the CI of the nIDEs increased over time as expected because the cell coverage of the nIDE increases over time. The calculated mean value of N=8 wells of nIDEs is represented by the square bullet point. A comparison to the data from Himmel et al., tracks the CI changes observed in our assay. Since our IDE pitch is 100× the pitch demonstrated by the IDE from Himmel, we believe the presence of the nanostructures result in 100× improvement in device sensitivity.

Figure 23:
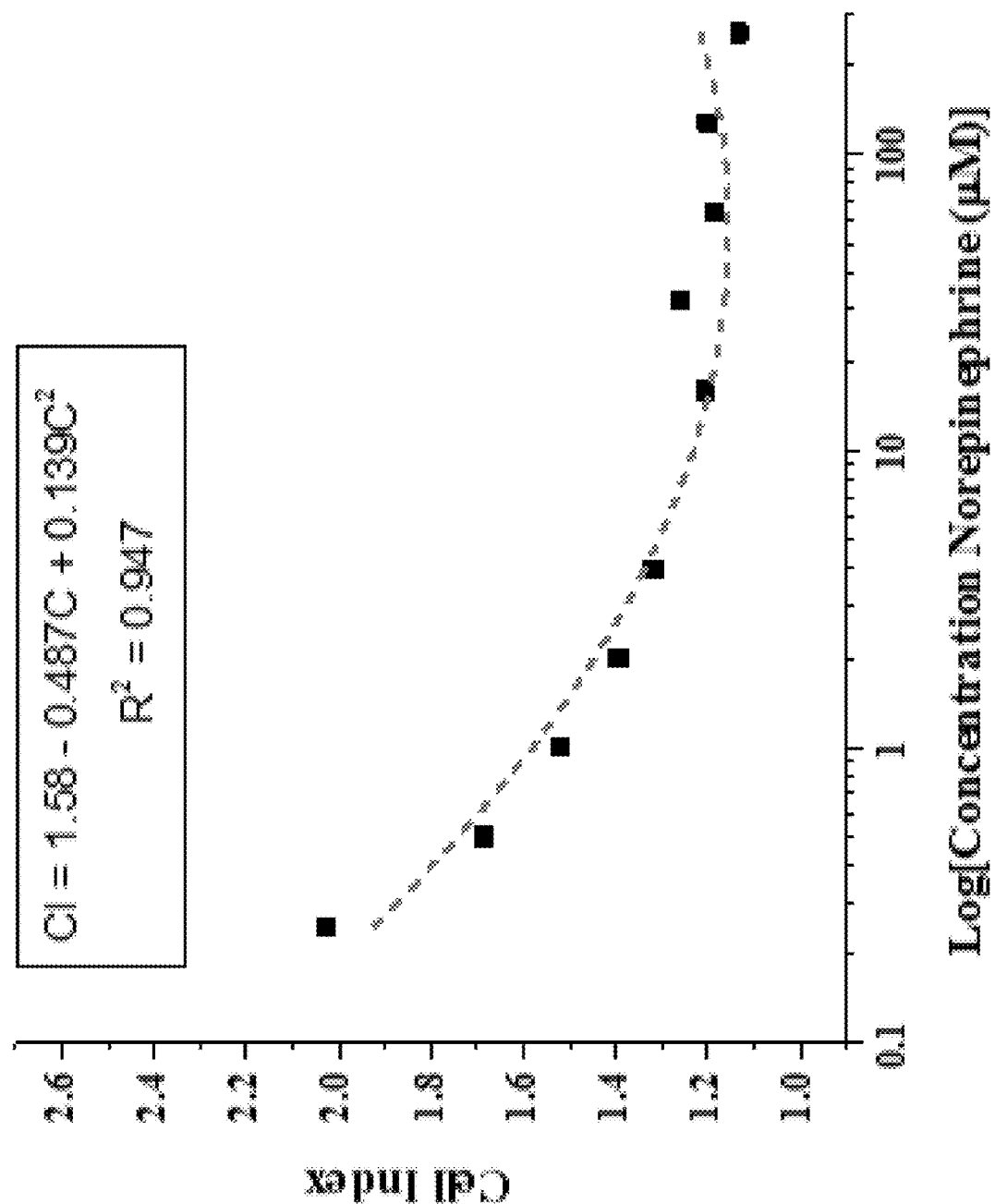
FIG. 23: is an example according to various embodiments, illustrating a chart showing the Cellular Index (CI) of the cardiomyocyte cells, referenced with respect to FIGS. 20 and 21.

FIG. 23 is an example according to various embodiments, illustrating a chart showing the Cellular Index (CI) of the cardiomyocyte cells, referenced with respect to FIGS. 20 and 21.

Figure 24:
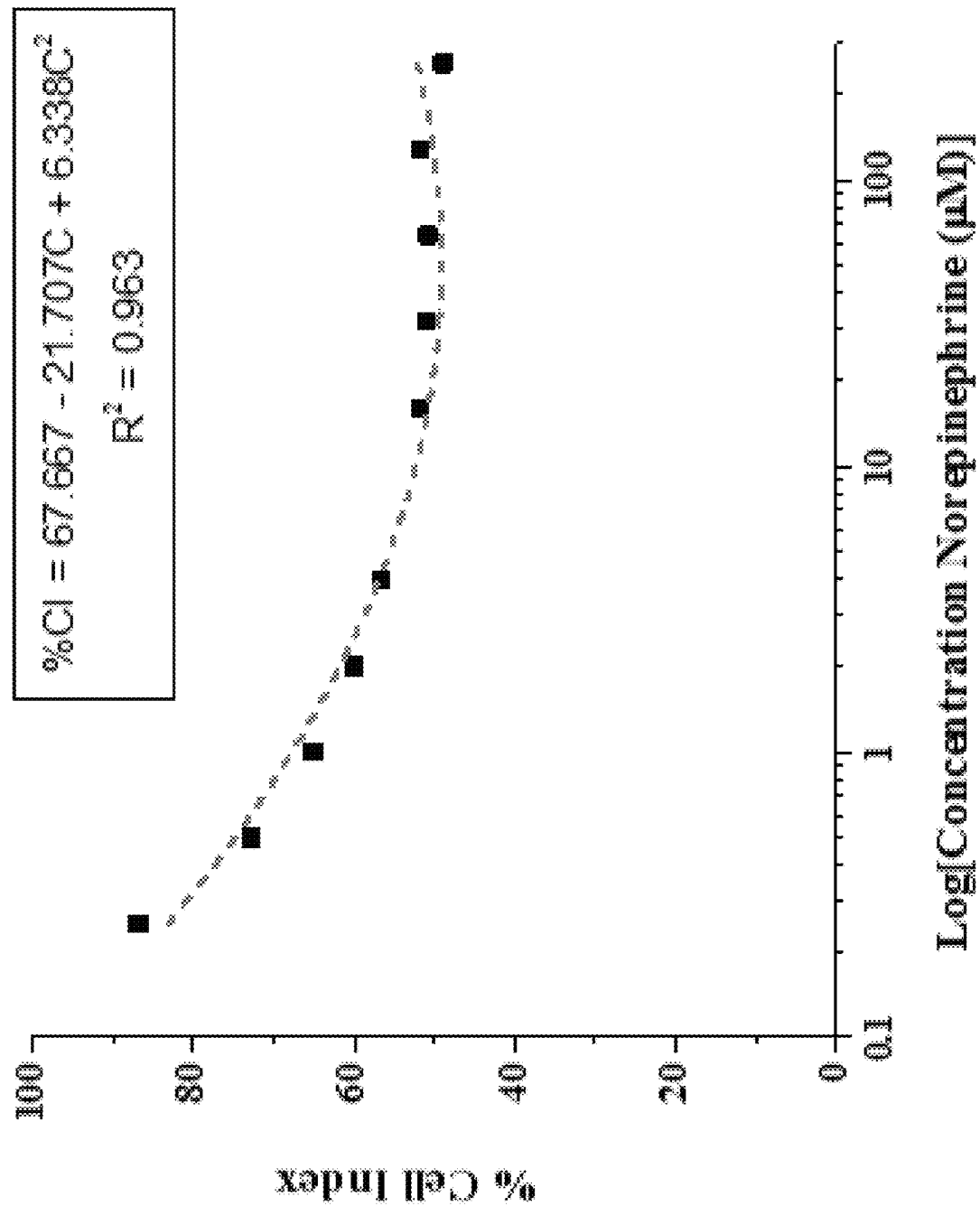
FIG. 24: is an example according to various embodiments, illustrating a chart showing percent Cellular Index (CI) of the cardiomyocyte cells, referenced with respect to FIGS. 20, 21, and 22.

FIG. 24 is an example according to various embodiments, illustrating a chart showing percent Cellular Index (CI) of the cardiomyocyte cells, referenced with respect to FIGS. 20, 21, and 22. FIG. 24 % CI for norepinephrine experiment: Mean values for N=6 is depicted with a square bullet point. The CI and % CI both decrease as the concentration of norepinephrine increases because the cells are dying due to the dosage of the drug. This causes a departure from the impedance of the nIDE with no norepinephrine added.

Nanostructured IDEs (nIDEs) were successfully fabricated on the nanostructured PAN substrates. The nanostructures on the PAN substrate remained defined after the deposition of the gold IDE structure, as shown in FIGS. 6, 7, and 8. FIG. 6 SEM image of electrodes deposited on top of the nanostructured PAN layer with zoomed in SEM images of the printed 50 nm PAN nanohole structures. Scales from left to right are FIG. 6 250 μm, FIG. 7 1 μm, and FIG. 8 180 nm respectively. These SEM micrographs clearly depict the nanostructured PAN with repeatable "nanoholes" of approximately 50 nm in diameter and the mm-scale gold electrodes defined on top of these "nanoholes". Fully assembled devices, as shown in FIG. 12, remained intact throughout the entire life cycle of the cardiomyocytes.

Human iPSC cardiomyocytes were successfully cultured onto the nIDEs (FIG. 15). FIG. 15 Human iPSC Cardiomyocytes cultured on 1 mm pitch nIDE at DIV01. The cardiomyocytes completely cover the surface of the IDE. One can clearly observe a mat of cells on top of the IDEs in the images collected with transmitted light microscopy. The cell viability assay confirmed that the nanostructured PAN substrate was cytocompatible for cell culture with cardiomyocytes. The other components of the nIDE (gold, PDMS, and 353ND epoxy), have previously been established to be cytocompatible with cardiomyocytes. Fluorescence levels were well above the background fluorescence, which indicates that most of the cultured cells were viable, as shown in FIG. 20. Quantitatively, the nanostructured PAN and control wells (N=6 for both types), both showed a fluorescence of nearly 40,000 RFU with a low standard deviation of approximately 3000 RFU, which depicts excellent cytocompatibility performance with iCell Cardiomyocytes[2].

FIG. 21 depicts the raw, full spectrum impedance data for polystyrene beads, iCell[2] cardiomyocytes (average value of N=8 at two specific days: DIV10 and DIV18), and aqueous media clearly delineating the three analytes. Further, this Figure shows that the impedance of the nIDEs with cells (110.19 kΩ at 1 kHz for DIV10 and 243.21 kΩ at 1 kHz for DIV18) and polystyrene beads (96.53 kΩ at 1 kHz) were higher than the nIDE with just aqueous medium (27.37 kΩ at 1 kHz), which follows expected trends due to the modification of the ionic currents due to the presence of cells. Looking closely at the ECIS for the two sample DIV measurements (N=8), they demonstrated an increase in impedance as the days in vitro increased. The cell index also demonstrated an increase as the days in vitro increased (FIG. 22). This is an expected result as reported by Himmel, et. al. because impedance is expected to increase as the cell coverage increases; and the cell coverage will inherently increase as the cells grow over time. This result with 1 mm pitch nIDEs over a period of 18 days with human cardiomyocytes is unique. The devices, according to various embodiments, are 100× larger than prior art devices, but report similar CI increases from cell growth (CI=0 on DIV10 increasing to CI equal to approximately 7-8 on DIV17) due to the nanoscale structure of the nIDEs. As a result, the nIDEs, according to various embodiments, may show a 100× increased sensitivity compared to commercial IDE systems.

The model drug experiment with norepinephrine showed a decrease in both cell index (from CI=2.34 at 0 μM of norepinephrine to CI=1.13 at 256 μm norepinephrine) (FIG. 23) and percent cell index (86.91% at 0 μM of norepinephrine to 48.88% at 256 μm norepinephrine) (FIG. 24) with increasing concentrations of norepinephrine (mean of N=7). This is expected because as the cardiomyocytes are exposed to higher concentrations of norepinephrine, more cells are expected to die from the exposure. As a result, there was less active cell coverage, which lowers the impedance, CI, and % CI.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

All patents, patent applications, provisional applications, and publications referred to or cited herein, supra or infra, are incorporated by reference in their entirety, including all figures and tables, to the extent they are not inconsistent with the explicit teachings of this specification.

It should be emphasized that the above-described embodiments of the present disclosure are merely possible examples of implementations and are merely set forth for a clear understanding of the principles of this disclosure. It should be understood that the examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure and protected by the following claims.

What is claimed is:

1. An interdigitated electrode device comprising
    interdigitated electrodes disposed on a nanostructured polymer layer, wherein the nanostructured polymer layer comprises a plurality of nanoholes, and wherein the interdigitated electrode device is plasmonic; and
    a culture well that is disposed on the interdigitated electrodes, wherein the culture well is coated with a biocompatible polymer.

2. The interdigitated electrode device of claim 1, wherein the interdigitated electrodes comprise a material selected from a noble metal, a semimetal, and combinations thereof.

3. The interdigitated electrode device of claim 1, wherein the nanostructured polymer layer comprises polyacrylonitrile (PAN).

4. The interdigitated electrode device of claim 1, wherein the plurality of nanoholes have an average diameter of from about 20 to about 300 nm.

5. The interdigitated electrode device of claim 1, wherein each of the plurality of nanoholes extends through a thickness of the nanostructured polymer layer.

6. The interdigitated electrode device of claim 5, wherein the thickness of the nanostructured polymer layer is from about 1 to about 20 μm.

7. The interdigitated electrode device of claim 1, wherein the plurality of nanoholes have a pitch of from about 50 to about 500 nm.

8. The interdigitated electrode device of claim 1, further comprising a transparent glass substrate, wherein the nanostructured polymer layer is disposed on the transparent glass substrate.

9. The interdigitated electrode device of claim 1, wherein the interdigitated electrodes have a pitch of 1 mm.

* * * * *